(12) United States Patent
Wang et al.

(10) Patent No.: US 7,354,928 B2
(45) Date of Patent: Apr. 8, 2008

(54) SMALL MOLECULE INHIBITORS TARGETED AT BCL-2

(75) Inventors: Shaomeng Wang, Saline, MI (US); Dajun Yang, Rockville, MD (US); Istvan J. Enyedy, Milton, MA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 45 days.

(21) Appl. No.: 10/286,085

(22) Filed: Nov. 1, 2002

(65) Prior Publication Data

US 2003/0199489 A1 Oct. 23, 2003

Related U.S. Application Data

(60) Provisional application No. 60/363,836, filed on Mar. 2, 2002, provisional application No. 60/330,865, filed on Nov. 1, 2001.

(51) Int. Cl.
*A61K 31/44* (2006.01)
*A61K 31/335* (2006.01)
*A61K 31/135* (2006.01)
*A61K 31/505* (2006.01)
*A61K 31/65* (2006.01)

(52) U.S. Cl. ............ 514/297; 514/648; 514/449; 514/274; 514/152; 514/27; 514/90; 424/617

(58) Field of Classification Search .......... 514/297, 514/648, 449, 274, 152, 27, 90; 424/617
See application file for complete search history.

(56) References Cited

U.S. PATENT DOCUMENTS

| | | | |
|---|---|---|---|
| 3,347,885 A | 10/1967 | Jones et al. | 260/412.4 |
| 3,364,242 A | 1/1968 | Johnson et al. | 260/420 |
| 3,647,791 A | 3/1972 | Rossi et al. | 260/268 |
| 4,297,341 A | 10/1981 | Waller et al. | 424/80 |
| 4,747,979 A | 5/1988 | Gimber et al. | 260/412.4 |
| 4,806,568 A | 2/1989 | Vander Jagt et al. | 514/522 |
| 5,026,726 A | 6/1991 | Jagt et al. | 514/468 |
| 5,059,717 A | 10/1991 | Ibragimov et al. | 568/438 |
| 5,077,441 A | 12/1991 | Kuk et al. | 568/761 |
| 5,112,637 A | 5/1992 | Hron, Sr. et al. | 426/629 |
| 5,260,327 A | 11/1993 | Kim et al. | 514/405 |
| 5,277,909 A | 1/1994 | Schmidt et al. | 424/195.1 |
| 5,385,936 A | 1/1995 | Flack et al. | 514/548 |

(Continued)

FOREIGN PATENT DOCUMENTS

CH 9710990 12/1987

(Continued)

OTHER PUBLICATIONS

Wu et al., J. Chromatography 433:141 (1988).

(Continued)

*Primary Examiner*—Shengjun Wang
(74) *Attorney, Agent, or Firm*—Casimir Jones, S.C.

(57) ABSTRACT

The present invention relates to small molecule antagonists of Bcl-2 family proteins such as Bcl-2 and/or Bcl-$X_L$. In particular, the present invention provides non-peptide cell permeable small molecules (e.g., tricyclo-dibenzo-diazocine-dioxides) that bind to a pocket in Bcl-2/Bcl-$X_L$ that block the anti-apoptotic function of these proteins in cancer cells and tumor tissues exhibiting Bcl-2 protein overexpression. In preferred embodiments, the small molecules of the present invention are active at the BH3 binding pocket of Bcl-2 family proteins (e.g., Bcl-2, Bcl-$X_L$, and Mcl-1). The compositions and methods of the present invention are useful therapeutics for cancerous diseases either alone or in combination with chemotherapeutic or other drugs.

20 Claims, 5 Drawing Sheets

Bcl-2 protein level

HL-60    MDA-231    T47D    MDA-453

U.S. PATENT DOCUMENTS

| | | | | |
|---|---|---|---|---|
| 5,464,833 | A | * | 11/1995 | Nakai et al. .................. 514/251 |
| 5,759,837 | A | | 6/1998 | Kahajda et al. ............. 435/193 |
| 5,780,675 | A | | 7/1998 | Royer et al. ................. 562/467 |
| 5,981,536 | A | * | 11/1999 | Mullner et al. ........ 514/263.31 |
| 6,114,397 | A | | 9/2000 | Flack et al. .................. 514/682 |
| 6,576,660 | B1 | | 6/2003 | Liao et al. ................... 514/456 |
| 6,608,107 | B2 | | 8/2003 | Wong et al. ................. 514/548 |
| 2002/0137801 | A1 | | 9/2002 | Wong et al. |
| 2003/0082101 | A1 | | 5/2003 | Taylor et al. |
| 2003/0119894 | A1 | | 6/2003 | Murthy et al. |
| 2005/0027000 | A1 | | 2/2005 | Reed et al. |

FOREIGN PATENT DOCUMENTS

| | | |
|---|---|---|
| CH | 1033795 A | 7/1988 |
| CH | 676360 A5 | 12/1988 |
| CH | 1044455 A | 8/1990 |
| CH | 1094392 A | 11/1994 |
| DE | 1 917 341 | 4/1969 |
| EP | 0 651 636 B1 | 7/1993 |
| FR | 2178204 | 3/1973 |
| JP | 01132542 A | 11/1987 |
| SU | 322042 A | 7/1969 |
| SU | 1351915 A1 | 6/1982 |
| SU | 2067111 | 5/1992 |
| WO | WO 94/20497 | 9/1994 |
| WO | WO 96/04250 | 2/1996 |
| WO | WO 97/40015 | 10/1997 |
| WO | WO 02/41828 A2 | 5/2002 |
| WO | WO 02/47673 A2 | 6/2002 |

OTHER PUBLICATIONS

Shen et al., Ch. J. Magnetic Resonance 20:373 (2003).
Meyers et al., Tetrahedron 54:10493 (1998).
Brzezinski et al., J. Mol. Structure 230:261 (1990).
Matlin et al., J. Liquid Chromotography 12:1485 (1989).
Jaroazewski et al., Chirality 4:216 (1992).
Przybylski et al, J. Mol. Structure 691:227 (2004).
Przybylski et al., J. Mol. Structure 654:167 (2003).
Przybylski et al., J. Mol Structure 569:147 (2001).
Haas et al., J. Org. Chem. 30:4111 (1965).
Przyblski et al., J. Mol. Structure 699:65 (2004).
Dao, Disssertation, University of Paris XI (2002).
Boyfield et al., "n-(substituted-phenyl)piperazines:" Bioorganic And Medicinal Chemistry Letters, 6:1227-32 (1996).
Rao, "Agents acting on the central nervous system. XIII:", Journal of Medicinal Chemistry 13:516-22 (1970).
Singh et al., "Antihypertensive and cas depressant properties of 3-(gamma-p-fluorobenzoylpropyl)2,3,4,4a,5,6-hexahydro-a)h)-pyrazinol(1-2-a)quinoline hydrochloride", Experientia 29:1529-30 (1973).
Singh et al., "Pharmacological studies on 3[gamma-(p-fluorobenzoly)propyl]-2,3,4,4a,5,6,hexahydro-1-(H)pyrazinol(1,2,-a)quinoline hydrochloride(Compound 69/83)" Arrzneimittel Forschung Drug Research 28:1641-4 (1978).
V. Amberger, et al., Cancer Res., 58:149-158 (1998).
Wick et al. (W. Wick, et al., FEBS Lett., 440:419-424 (1998).
S. Mohanam, et al., Cancer Res. 53:4143-4147 (1993).
P. Pedersen, et al., Cancer Res., 53:5158-5165 (1993).
Nuria Rubio, Lab Invest, 81:725-734 (2001).
Fernández et al., Cell Death Differ., 7:350-359 (2000).
J. Reed, Nature, 387:773-776 (1997).
S. Frisch and E. Ruoslahti, Curr. Opin. Cell Biol., 9:701-706 ((1997).
D. Del Bufalo, et al., FASEB J., 11:947-953 (1997).
Razakantoanina et al. Parasitol. Res., 86:665-668 (2000).
Dao et al. Bioorg. Med. Chem., 11:2001-2006 (2003).
Deck et al. J. Med. Chem., 34:3301-3305 (1991).
Przybylski et al. J. Mol. Structure, 611(1-3):193-201 (2002).
R.E. Royer et al., J. Med. Chem., 38:2427-2432 (1995).
R.E. Royer et al., Biologically active derivativse of gossypol: synthesis and antimalarial activities of peri-acylated gossylic nitriles:, J. Med. Chem., 29:1799-1801 (1986).
C.M. Venuti, J. Org. Chem., 46(15):3124-3127 (1981).
P.C. Meltzer et al., J. Org. Chem., 50(17):3121-3124 (1985).
R. Adams et al., J. Am. Chem. Soc., 60:2193-2204 (1938).
Le Blanc et al. "An in vitro study of inhibitory activity of gossypol, a cottonseed extract, in human carcinoma cell lines", Pharmacol. Res., 46:551-555 (2002).
Baumgrass et al., "Reversible inhibition of calcineurin by the polyphenolic aldehyde gossypol", J. Biol. Chem., 276:47914-47921 (2001).
Shelley et al., "Structure-activity studies on gossypol in tumor cell lines," Anticancer Drugs, 11:209-216 (2000).
Sonenberg et al., "Anti-fertility and othe ractions of gossypol analogues", Contraception, 37:247-255, (1988).
Whaley et al, "Monkey lactate dehydrogenase-C4 as model for the interaction of enzymes with gossypol", Contraception, 33:605-616 (1986).
Dorsett et al., "Letter: Antivrial activity of gossypol and apogossypol", J. Pharm. Sci., 64:1073-1075 (1975).
Wu et al., "Synthesis and antifertility actions of gossypol derivatives and phenol aldehydes", Yao Xue Xue Bao, 24:502-511 (1989).
Hoffer et al., "Antifertility, spermicidal and ultrastructural effects of gossypol and derivatives administered orally and by intratesticular injections", Contraception, 37:301-331 (1988).
Guo et al., "Synthesis of mono-aldehyde gossypol and its analogues", Yao Xue Xue Bao, 22:597-602 (1987).
Manmade et al., "Gossypol. Synthesis and in vitro spermicidal activity of isomeric hemigossypol derivatives", Experientia, 39:1276-1277 (1983).
Dowd, Chirality, 15:486 (2003).
Ciesielska et al., Chem. Phys. Lett. 353:69 (2002).
Vermel et al., Antitumour Activity of Gossypol in Experiments on Transplanted Tumours 39-43 (1963).
Freedman et al., Chirality, 15:196 (2003).
J.C. Reed, Pharmacology, 41:501-533 (1997).
J.C. Reed et al., J. Cell Biochem., 6:23-32 (1996).
Z. Han et al., Cancer Res., 56:621-628 (1996).
S.W. Muchmore et al., Nature, 381:335-341 (1996).
A.M. Petros et al., Protein Sci., 9:2528-2534 (2000).
A.M. Petros et al., Proc. Natl. Acad. Sci. U.S.A., 98:3012-3017 (2001).
X.M. Yin et al., Nature, 369:321-323 (1994).
S.C. Cosulich et al., Curr. Biol., 7:913-920 (1997).
A. Sali et al., Structure, Function, and Genetics, 23:318-326 (1995).
A. Sali, Curr. Opin. Biotech., 6:437-451 (1995).
J.L. Wang et al., Cancer Res., 60:1498-1502 (2000).
J.L. Wang et al., Proc. Natl. Acad. Sci. U.S.A., 97:7124-7129 (2000).
Sattler et al., Science, 275:983-986 (1997).
B.R. Brooks et al., J. Comp. Chem., 4, 187-217 (1983).
P.V.R. Schleyer et al., CHARMM: The Energy Function and Its Parameterization with an Overview of the Program, in The Encyclopedia of Computational Chemistry, 1:271-277 eds., John Wiley & Sons, Chichester (1998).
S. Makino and I.D. Kuntz, J. Comput. Chem. 18:1812-1825 (1997).
I.J. Enyedy et al., J. Med. Chem., 44:313-4324 (2001).
Leschev, "Influence of the Extract of Eleutherococcus senticosus on development of experimental pituitary adenomas in rats", Institute of Oncology of the U.S.S.R. Academy of Medical Sciences, 60-67 (1966).
Willemsen, An Oxazoline-Based Approach to the Total Asymmetric Synthesis of (S)-Gossypol, UMI PROQuest Digial Disserations—Full Citation & Abstract.
La Blanc et al., An in vitro study of inhibitory activity of gossypol, a cottonseed extract, in human carcinoma cell lines, Pharmacol. Res. 46(6):551-5 (2002).
Griffith et al., Bioenvision Successfully Completes Formulation Research to Develop Gossypol as a Novel Anti-Cancer Agent, Bioenvision News (2003).
Saydachmov et al., Uebekskii Khimicheski Zhurnal (1):11-13 (1994).

Zakhidov et al., Modifying Cytogenetic Effects of Gossypol and Derivatives, Library National Institutes of Health (1994).

Erukhimov, Treatment of Bladder Tumors With Gossipol And Ionol In Combination With Surgical Intervention, Issues in Oncology, XI (1966).

Kuznezova et al., Pharmacol. Toxicol., Boston Library Boston Spa (1979).

Zhong et al., National Library of Medicine, 2:159-161 (1982).

Zhang et al., Inhibitory effects (-)-gossypol on proliferation and keratinocyte growth factor expression in human breast epithelial cells, stromal cells, and adipocytes, American Association fro Cancer Research 38:218 (1997).

Zheng et al., Gossypol (GP) Stimulates Transforming Growth Factor Beta (TGF-β) Gene Expression in Human Breast Cancer Cell Line, The FASEB Journal 10:A757 (1996).

Zheng et al., Studies on the Resolution of Racemic Gossypol, ACTA Pharmaceutica Simica 25(6):430-434 (1990).

Adlakha et al., Inhibition of DNA Polymerase α And Ribonucleotide Reductase by By Gossypol, Proceedings of AACR 26:249:982 (1985).

Akhila et al., Biosynthesis of Gossypol in *Thespesia populnea*, Phytochemistry 33:335-340 (1993).

Badria et al., Antimitotic Activity of Gossypol and Gossypolone, Pharmaceutical Biology, 39:120-126 (2001).

P. Baille et al., Clin. Cancer Res., 3:1535-1538 (1997).

Balci et al., Gossypol induced apoptosis in the human promyelocytic cell line HL60, Cytogenet Cell Genet 85:5-181 (1999).

Balci et al., Gossypol Induced Apoptosis in the Human Promyelocytic Leukemia Cell Line HL 60, Tohoku J. Exp. Med. 189:51-57 (1999).

Band et al., Antiproliferative Effect Of Gossypol and Its Optical Isomers on Human Reproductive Cancer Cell Lines, Gynecologenic Oncology 32:273-277 (1989).

Band et al., Cytocidal Effects of Gossypol and Its Optical Isomers on Reproductive Cancer Cell Lines,Gynecologic Oncology 23:261 (1986).

Benz et al., Lactic Dehydrogenase Isozymes, $^{31}$P Magnetic Resonance Spectroscopy, and In Vitro Antimitochondrial Tumor Toxicity with Gossypol and Rhodamine-123, J. Clin.Invest. 79:517-523 (1987).

Benz et al., Selective Toxicity of Gossypol Against Epithelial Tumors and its Detection by Magnetic Resonance Spectroscopy, Contraception 37:221-229 (1988).

Benz et al., Gossypol Enantiomers (+,-) Differentially Uncouple Tumor Mitochondria, Block Glutathione-S-Transferase Activity, and Inhibit Cellular Proliferation, Proceedings of AACR 29:322 (1988).

Benz et al., Biochemical Correlates of the Antitumor and Antimitochondrial Properties of Gossypol Enantiomers, Molecular Pharmacology 37:840-847 (11990).

Benz et al., Gossypol Effects of Endothelial Cells and Tumor Flow, Life Sciences 49:67-72 (1991).

Blackstaffe et al., Cytotoxicity of gossypol enantiomers and its quinone metabolite gossypolone in melanoma cell lines, Melanoma Research 7:364-372 (1997).

Bourinbaiar et al., Comparative in vitro study of contraceptive agents with anti-HIV activity: *Gramicidin, nonoxynol-9, and gossypol,* Contraception 49:131-137 (1994).

Brandes et al., New Drugs in Recurrent High Grade Gliomas, Anticancer Research 20:1913-1920 (2000).

Brandes et al., New therapeutic agents in the treatment of recurrent high-grade gliomas, FORUM Trends in Experimental and Clinical Medicine 10:121-131 (2000).

R. Bruno et al., J. Clin. Oncol., 16:187-196 (1998).

Bushunow et al., Gossypol Treatment of Recurrent Adult Malignant-Gliomas, Proceedings of ASCO, 14:282 (1995).

Bushunow et al., Gossypol Treatment of recurrent adult malignant gliomas, Journal of Neuro-Oncology 43:79-86 (1999).

Chang et al., Antiproliferative and Antimetastatic Effects of Gossypol (GP) on Mat-Lylu-Bearing Rats, FASEB Journal, 6:3794 (1992).

Chang et al., Prostate, begin hypertrophy and prostatic carcinoma: A study of cell biology of prostate and chemotherapy for prostatic hypertrophy and prostatic cancer, Dissertation Abstract International, 55:4330-B (1995).

Chang et al., Potential of Gossypol (GP) and Transforming Growth Factor-β, (TGF-β$_1$) as Inhibitors of Canine Prostate Growth, FASEB Journal, 9:4813-4814 (1995).

Chang et al., Antiproliferative and Antimetastatic Effects of Gossypol on Dunning Prostate Cell-Bearing Copenhagen Rats, Research Communications in Chemical Pathology and Pharmacology 79:293-312 (1993).

Chen et al., Application of 2D NMR Techniques in the Structure Determination of Ganosporelactone A and B, ACTA Pharmaceutica Simica 26:430-436 (1991).

Coyle et al., *In-Vitrop* and *in vivo* cytotoxicity of gossypol against central nervous system tumor cell lines, Journal of Neur-Oncology 19:25-35 (194).

Dallacker et al., Uber Gossypol- und Hemigossypol-Derivate—Darstellung von Hydroxy-methyl-naphto[1,3]dioxolen, Chemiker-Zeitung 113:5-11 (1989).

Dallacker et al., Darstellung von Methyl-isopropyl-naphthol-derivaten durch Pd-katalysierte Cyclocarbonylierung, Chemiker-Zeitung 114:144-147 (1990).

Dao et al., Synthesis and cytotoxicity of gossypol related compounds, Eur. J. Med. Chem. 35:805-813 (2000).

Darzynkiewicz et al., Cytometry in Cell Necrobiology: Analysis of Apoptosis and Accidental Cell Death (Necrosis), Cytometry 27:1-20 (1997).

Data et al., A Study of the Derivatives of (±)-Gossypol, Indian Journal of Chemistry 10:691-693 (1972).

Davila et al., Toxicological Studies of Gossypol in Primary Culture of Postnatal Rat Hepatocytes, Journal of Molecular and Cellular Toxicology, 4:161-170 (1991).

Deck et al., Gossypol and Derivatives: A New Class of Aldose Reductase Inhibitors, J. Med. Chem. 34:3301-3305 (1991).

DeMartino et al., Electron microscopic and biochemical studies of the effect of Gossypol on Ehrlich ascites tumor cells, Caryologia, International Journal of Cytology, Cytosystematics and Cytogenetics 35:114-115 (1982).

de Peyster et al., Genetic toxicity studies of gossypol, Mutation Research 197:293-312 (1993).

De-yu et al., Mutagenicity of gossypol analyzed by inductio of meiotic micronuclei in vitro, Mutation Research 208:69-72 (1988).

Dhaliwal et al., Cytogenetic Analysis of a Gossypol-Induced Murine Myxosarcoma, Journal of the National Cancer Institute, 78:1203-1209 (1987).

A. Degterev et al., Nat. Cell Biolog., 3:173-182 (2001).

Dogliotti et al., Cytotoxic chemotherapy for adrenocortical carcinoma, Minerva Endocrinologica, 20:105-109 91995).

Edwards et al., Sysnthesis of Gossypol and Gossypol Derivatives, Journal of the American Oil Chemists' Society 47:441-442 (1970).

Finaly et al., Mechanism of the Gossypol Inactivation of Pepsinogen, Journal of Biological Chemistry 248:4827-4833 (1973).

Fish et al., The Photo-epimerisation of Gossypol Schiff's Bases, Tetrahedron: Asymmetry 6:873-876 (1995).

Flack et al., Treatment of adrenocortical carcinoma with gossypol, Proceedings of American Association for Cancer Research 31:198 (1990).

Flack et al., Oral Gossypol in the Treatment of Metastatic Adrenal Cancer, Journal of Clinical Endocrinology and Metabolism, 76:1019-1024 (1993).

Floridi et al., The Effect of the Association of Gossypol and Lonidamine on the Energy Metabolism of Ehrlich Ascites Tumor Cells, Experimental and Molecular Pathology 38:322-335 (1983).

Floridi et al., The Effect of Gossypol and Lonidamine on Electron Transport in Ehrlich Ascites Tumor Mitochondria, Experimental and Molecular Pathology 40:246-261 (1984).

Ford et al., Modulatio nof resistance of alkylating agents in cancer cell by gossypol enantiomers, Cancer Letters 56:85-94 (1991).

Gilbert et al., Antiproliferative Activity of Gossypola nd Gossypolone on Human Breast Cancer Cells, Life Sciences 57:61-67 (1995).

Gonzalez-Garza et al., Cytotoxic Effects of Gossypol and Vitamin E on Human and Rat Lymphocytes and Spermatozoa, Nutrition Reports International (1995).

Gorczyca et al., The Cell Cycle Related Differences in Susceptibility of HL-60 Cells to Apoptosis Induced by Various Antitumor Agents, Cancer Research 53:3186-3192 (1993).

Grankvist, Gossypol-Induced Free Radical Toxicity to Isolated Islet Cells, Int. J. Biochem. 21:853-856 (1989).

Hamasaki et al., Gossypol, a potent inhibitor of arachidonate 5- and 12-lipoxygenases, Biochimica et Biophysica Acta 834:37-41 (1985).

Han et al., Gossypol in the Treatment of Endometriosis and Uterine Myoma, Chontr. Gynec. Obstet. 16:268-270 (1987).

Haroz et al., Tumor Initiating And Promoting Activity of Gossypol, Toxicology letters, 72 (1980).

Haspel et al., Cytocidal Effect of Gossypol on Cultured Murine Erythroleukemia Cells is Prevented by Serum Protein, Journal of Pharmacology and Experimental Therapeutics 229:218-225 (1984).

J. Hirth et al., Clin. Cancer Res., 6:1255-1258 (2000).

Heinstein et al., The Biosynthesis of Gossypol, Biochemistry 28:1342-B (1967).

Hendricks et al., Hepatocarcinogenicity of Glandless Cottonseeds and Cottonseed Oil to Rainbow Trout (*Salmo gairdnerii*), Science 208:309-311 (1980).

Herve et al., Contraceptive gossypol blocks cell-to-cell communication in human and rat cells, European Journal of Pharmacology 313:243-255 (1966).

Hong et al., Study of the Effects of Acetate Gossypol, High Energy Shock Waves (HESW) and Their Combination on the Human Bladder Cancer Cell Line $BT_{5637}$, ACTA Anatomica Sinica 25:291-296- (1994).

Hu et al., Gossypol Effects on Cultured Normal and Malignant Melanocytes, In Vitro Cellular & Development Biology 22:583-588 (1986).

Hu et al., Gossypol Inhibits Basal And Estrogen ($E_2$)-Stimulated DNA Synthesis in Human Breast Carcinoma (HBC) Cells, FASEB Journal, 7:3982 (1993).

Hu et al., Gossypol Inhibits Basal And Estrogen-Stimulated DNA Synthesis in Human Breast Carcinoma Cells, Life Sciences 53:433-439 (1993).

Hu et al., Presence of antitumor activities in the milk collected from gossypol-treated dairy cows, Cancer Letters 87:17-23 (1994).

Huang et al., Resolution of Racemic Gossypol, Journal of Ethnopharmacology 20:13-20 (1987).

Huchinson et al., The mechanism of gossypol acetic acid cytotoxicity, Dissertation Abstracts Inernational, 59:1612-B (1998).

Hutchinson et al., Attenuation of Gossypol Cytotoxicity by Cyclic AMP in a Rat Liver Cell Line, Toxicology and Applied Pharmacology 151:311-318 (1998).

Jaroszweski et al., Action of Gossypol and Rhodamine 123 on Wild type and Multidrug-resistant MCF-7 Human Breast Cancer Cells: $^{31}P$ Nuclear Magnetic Resonance and Toxicity Studies, Cancer Research 50:6936-6943 (1990).

Jarvis et al., INduction of Apoptotic DNA Fragmentation and Cell Death in HL-60 Human Promyelocytic Leukemia Cells by Pharmacological Inhibitors of Protein Kinase $C^1$, Cancer Research 54:1707-1714 (1994).

Jiang et al., Inhibitory Action of Gossypol on the Growth of MAT-LyLu Prostate Cancer Cells is Associated with Stimulation of Transforming Growth Factor-$\beta_1$ (TGF-$\beta_1$), Biology of Reproduction 60:252.

Jiang et al., Differing Effects of Gossypol on MAT-LYLU Cells and MAT-LYLU Cells Isolated From Metastasized Lung of MAT=LYLU Cell-Bearing Copenhagen Rats, Society for the Study of Reproduction 58:89.

Jiang et al., The Efffects of Gossypol on the Invasiveness of MAT-LyLu Cells and MAT-LyLu Cells from the Metastasized Lungs of MAT-LyLu Bearing Copenhagen Rats, Anticancer Research 20:4591-4598 (2000).

Jia-xin et al., Studies on the Synthesis of Gossypol Derivatives and Their Antifertility Action, Reproduction and Contraception 6:48-51 (1986).

Joingfang et al., Of Gossypol in Mice, Rats and Human Tumor Cell Lines and Its Possible Mechanism, ACTA Academiae Medicinae Sinicase 8:486-488 (1986).

Jolad et al., Tumor-Inhibitory Agent from *Montezuma speciosissima* (Malvaceae), Journal of Pharmaceutical Sciences 64:1889-1890 (1975).

Joseph et al., Cytotoxicity of enantiomers of gossypol, Br. J. Cancer 54:511-513 (1986).

Jung et al., Recent Studies on Natural Products as Anti-HIV Agents, Current Medicinal Chemistry 7:649-651 (2000).

Kai et al., Resolution of Racemic Gossypol, J. Chem. Soc., Chem. Commun. 3:168:169 (1985).

Kaplan et al., Metabolism of breast cancer cells as revealed by non-invasive magnetic resonance spectroscopy studies, Breast Cancer Research and Treatment 31:285-299 (1994).

Keller et al., Novel pharmacophore-based methods reveal gossypol as a reverse transcriptase inhibitor, Journal of Molecular Graphics and Modelling 5346:1-9 92002).

Keniry et al., Magnetic Resonance Spectroscopy (MRS) and Imaging (MRI) in the Evaluation of Tumor Growth and Chemotherapy Response, Proceedings of AACR 27:384 (1986).

Keniry et al., The Effect of Gossypola nd 6-Aminonicotinamide on Tumor Cell Metabolism: A $^{31}P$-Magnetic Resonance Spectroscopic Study, Biochemical and Biophysical Research Communications 164:947-953 (1989).

Kim et al., Comparative *In Vitro* Spermicidal Effects of (±)-Gossypol, (+)-Gossypo, (−)-Gossypol and Gossypolone, Contraception 30:253-259 (1984).

Koll et al., A Phase I Study of Gossypol (GP) in HIV-Infected Patients (pts) in Mexico, Abstracts of the 33rd ICAC 245-687.

Koryakin et al., Ultrasound investigation of blood supply in scrotal organs, 10th World Congress on Human Reproduction 307 (1999).

Latronico et al., Extensive Personal Experience Adrenocortical Tumors, Journal of Clinical Endocrinology and Metabolism 82:1317-1324 (1997).

LaVoie et al., Investigation of Intracellular Signals Mediating the Anti-Apoptotic Action of Prolactin in Nb2 Lymphoma Cells, Society for Experimental Biology and Medicine 257-269 (1995).

Lee, Novel Antitumor Agents from Higher Plants, Medical Research Reviews, 19:569-596 (1999).

Lee et al., Plant PHenolic Compounds as Cytotoxic Antitumor Agents, American Chemical. Society 29:367-369 (1992).

Lefeng et al., Clinical Effects and Experimental Study on Gossypol in Endometriosis, Chin. J. Integr Med. 9(8):451-464 (1989).

Levine, Inhibition of the A-23187-Stimulated Leukotriene And Prostaglandin Biosynthesis of Rat Basophil Leukemia (RBL-1) Cells By Non-Steroidal Anti-Inflammatory Drugs, Anti-Oxidants, and Calcium Channel Blockers, Biochemical Pharmacology 32:3023-3025 (1983).

Li et al., DNA-Breaking Versus DNA-Protecting Activity of Four Phenolic Compounds *in vitro*, Free Rad. Res. 33:551-566 (2000).

Lian et al., Hepatoma Initiating and Promoting Effects of Gossypol, ACTA Academiae Medicinae Sinicase (1985).

Liang et al., Developing gossypol derivatives with enhanced antitumor activity, Investigational New Drugs 13:181-186 (1995).

Liqueros et al., The antiproliferative Effects of Gossypol and the Retinoblastoma Gene Protein, Clinical Pharmacology & therapeutics 57:206 (1995).

Liqueros et al., Gossypol inhibition of mitosis, cyclin D1 and Rb protein in human mammary cancer cells and cyclin-D1 transfected human fibrosarcoma cells, British Journal of Cancer 76:(1):21-28 (1997).

Lin et al., Selective Inhibition of Human Immunodeficiency Virus Type I Replication by the (−) but Not the (+) Enantiomer of Gossypol, Antimicrobial Agents and Chemotherapy, 2149-2151 (1989).

Lin et al., Anti-HIV-1 Activity and Cellular Pharmacology of Various Analogs of Gossypol, Biochemical Pharmacology 46:251-255 (1993).

Lin et al., Gossypol and tamoxifen prevent estrogen-induced renal carcinogenesis in hamsters, Proceedings of the American Association for Cancer Research 36:391-2329 (1995).

Majumdar et al., Genotoxic Effects of Gossypol Acetic Acid on Cultured Murine Erythroleukemia Cells, Environmental and Molecular Mutagenesis 18:212-219 (1991).

Matlin et al., Large-Scale Resolution of Gossypol Enantiomers for Biological Evaluation, Contraception 37:229-237 (1988).

McSheehy et al., Gossypol, a cytoxic agent, may uncouple respiration of Ehrlich ascites tumour cells, Biochemical Society Transactions 16:616-617 (1988).

Meiling, Gossypol Treatment for Menopausal Functional Bleeding, Myoma of Uterus and Endometriosis—Prelimnary Report, ACTA Academiae Medicinae Sinicae 2:167-169 (1980).

Meltzer et al., A Regioselective Route to Gossypol Analogues: The Synthesis of Gossypol and 5,5'-Didesisopropyl-5,5'-diethylgossypol, J. Org. Chem. 50:3121-3124 (1985).

Fujii et al., "Effect of cerulenin, an inhibitor of fatty acid synthesis, on the immune cytolysis of tumor cells" Jpn. J. Exp. Med Jun. 1986;56(3):99-106 (Abstract only).

Gossypol, Xian Oil 7 Fat Works, Drugs of the Future, vol. 21, No. 5, 1996.

Meyers et al., The synthesis of (S)-(+)-gossypol via an asymmetric Ullmann coupling, Chem. Commun., 1573-1574 (1997).

Moh et al.., Effect of Gossypol (GP) on a 5α-Reductase and a 3α-Hydroxysteroid Dehydrogenase (3α-HSD) in Adult Rat Tests, FASEB Journal 6342 (1992.

Mohan, Problems and Perspectives in the Design of Anti-HIV-1 Agents, Drug Development Research 29:1-17 (1993).

S.W. Muchmore et al., Nature, 381:335-341 (1996)). ,and.

Mushtaq et al., Gossypol (GP) Inhibits in Vitro Porcine Oocyte Maturation and Early Embryonic Development in Modified Simple Media, Society for the Study of Reproduction, 52:172 (1998).

Naik et al., Preclinical studies of gossypol in prostate carcinoma, Internatioanl Journal of Oncology 6:209-213 (1995).

Nayak et al., Induction of Sister Chromatid Exchanges and Chromosome Damage by Gossypol in Bone Marrow Cells of Mice, Teratogenesis, Carcinogenesis, and Mutagenesis 6:83-91 (1986).

Newman et al., Pharmacokinetics and toxicity of 120-hour continuous-infusion hydroxyurea in patients with advanced solid tumors, Cancer Chermother Pharmacol 39:254-258 (1997).

Ng et al., Anti-Human Immunodeficiency virus (ANTI-HIV) Natural Products with Special Emphasis on HIV Reverse Transcriptase Inhibitors, Life Sciences 61:933-949 (1997).

Ognyanov et al., Synthesis of Gossypol Analogues, Helvetica Chimica ACTA 72:353-360 (1989).

Ohuchi et al., Inhibition of gossypol of tumor promoter-induced arachidonic acid metabolism in rat peritoneal macrophages, Biochimica et Biophysica Acta, 971:85-91 (1988).

Olgiati et al., Gossypol Inhibition of Adenylate Cyclase, Archives of Biochemistry and Biophysics 231:411-415 (1984).

Papageorgiou et al., A New Method for the Isolation of Gossypol From Cottonseed-Oil Fatty Acids, Chimika Chronika 7:101-109 (1978).

Perez et al., Studies on spermatogenesis and apoptosis in the bovine, Disseration Abstracts International 50:526-B (1999).

Phung et al., Isolation and Purification of Gossypol in Cotton Seeds of Vietnam, Tap chi Hoa hov, 35:91-93 (1997).

Pirogov et al., Postoperative Bronchopleural Complications in Combined Treatment of Pulmonary Cancer, Issues of Oncology, 20:24-28 (1974).

Polsky et al., Inactivation of Human Immunodeficiency Virus (RIV) By Gossypol (GP), Clinical Research 35(3)487A (1987).

Polsky et al., Inactivation of Human Immunodeficiency Virus in Vitro By Gossypol, Contraception, 39:579-587 (1989).

Przybylski et al., Spectroscopic studies and PM5 semiempirical calculations of new Schiff bases of gossypol with amino derivatives of crown ethers, Journal of Molecular Structure, 16:04-1-9 (2002).

Qian, Gossypol: A Potential Antifertility Agent for Males, Ann. Rev. Pharmacol. Toxicol. 24:329-60 (1984).

Qui et al., The Search for Gene(s) Conferring Sensitivity to Cell Killing by Gossypol, The FASEB Journal 13:A151A (1999).

J. O'Quigley et al., Biometrics 46:33-48 (1990).

Quintana et al., Gossypol-induced DNA breaks in rat lymphocytes are secondary to cytotoxicity, Toxicology Letters 117:85-94 (2000).

Rao et al., Antitumor effects of gossypol on murine tumors, Cancer Chemother Pharmacol. 15:20-25 (1985).

Razakantoanina et al., Antimalarial activity of new gossypol derivatives, Parasitol Res. 86:665-668 (2000).

Reidenberg, Studies of gossypol in the treatment of cancer, Reproductive Medicine, 305-308.

Reidenberg et al., Gossypol Treatment of Metastatic Adrenal Cancer, Clinical Pharmacology and Therapeutics, 51:PI-96 (1992).

Rekha et al., Inhibition of Human Class 3 Aldehyde Dehydrogenase, and Sensitization of Tumor Cells that Express Significant Amounts of this Enzyme to Oxazaphosphorines, by the Naturally Occurring Compounds Gossypol, Enzymology and Molecular Biology of Carbonyl Metabolism 6, 133-146 (1996).

Resnick et al., Comparative Evaluation of Sperimicidal Agents with Virucidal Activity Against HIV, IXth International Conference on AIDS, 11:PO-C22-3154 (1993).

Rosenberg et al., Biochemical Basis for the Gossypol-indiced Inhibition of DNA Replication in Mammalian Cells, American Association for Cancer Research, 29:1291 (1988).

Royer et al., Inhibition of Human Immunodeficiency Virus Type I Replication by Derivatives of Gossypol, Pharmacological Research, 24:407-412 (1991).

G. Rassidakis et al., Amer. J. Path., 159:527-535 (2001).

J.C. Reed et al., Ann. Oncol., 5:61-65 (1994).

Sampath et al., A Rapid Procedure for the Resolution of Racemic Gossypol, J. Chem. Soc., Chem. Commun., 649-650 (1986).

Schinazi et al., Insights Into HIV Chemotherapy, Aids Research and Human Retroviruses, 8:963-990 (1992).

A.F. Schott et al., Oncogene, 11:1389-1394 (1995).

Seidman et al., Gossypol in Advanced Breast Cancer, Journal of Investigative Medicine 46:213A (1998).

Seidman, Chemotherapy for Advanced Breast Cancer: A Current Perspective, Seminars in Oncology, 23:55-59 (1996).

Shelly et al., Stereo-specific cytotoxic effects of gossypol enantiomers and gossypolone in tumour cells lines, Cancer Letters, 135:171-180 (1999).

Shelly et al., Structure-activity studies on gossypol in tumor cell lines, Anti-Cancer Drugs, 11:209-216 (2000).

S. Shi et al., J. Histochem. Cytochem., 39:741-748 (1991).

Shidaifat et al., Differential regulation of gene expression by gossypo0l: A potential inhibitor of prostate cell growth, Dissertation Abstracts International, 57:6097-B (1997).

Shidaifat et al., Inhibition of human prostate cancer cells growth by gossypol is associated with stimulation of transforming growth factor-β, Cancer Lettesr 107:37-44 (1996).

Shidaifat et al., Gossypol Arrests Human Benign Prostatic Hyperplastic Cell Growth at G0/G1 Phase of the Cell Cycle, Anticancer Research 17:1003-1010 (1997).

Sinnhuber et al., Dietary Factors and Hepatoma in Rainbow Trout (*Salmo gairdneri*). π. Cocarcinogenesis by Cyclopropenoid Fatty Acids and the Effect of Gossypol and Altered Lipids on Aflatoxin-Induced Liver Cancer, Journal of the National Cancer Institute, 41:1293-1299 (1968).

Stein et al., A preliminary clinical study of gossypol in advanced human cancer, Cancer Chemother Pharmacol 30:480-481 (1992).

Sugimoto et al., Differential proliferative rseponses to the (-)-enantiomer of gossypol in cultured human breat epithelial and stromal cells, American Association for Cancer Research 40:4 (1999).

Tai, Rat Basophilic Leukemia-1 Cell Possesses 12-Lipoxygenase and 5-Lipoxygenase activites which are specifically inhiibited by gossypol acetic acid, Japanese Journal of Allergology 33:1040-1046 (1984).

Tan et al., Evaluation of Natural Products As Inhibitors of Human Immunodeficiency Virus Type 1 (HIV-1) Reverse Transcriptase[1], Jouranl of Natural Products, 54:143-154 (1991).

Tanphaichitr et al., Direct Effect of Gossypol on TR-ST Cells: Pertubation of Rhodamine 123 Accumulation in Mitrochondria, Biology of Reproduction, 31:1049-1060 (1984).

Tao et al., The Effects of Gossypol on Human BPH Cells In Vitro, 21:31 (1994).

Teng et al., c-MYC Protein Expression in spermatocytes During Gossylpol-Induced Apoptosis, Molecular Biology of the Cell, 364a:2116 (1997).

Teng et al., Biphasic c-Myc Protein Expression During Gossypol-Induced Apoptosis in Rat Spermatocytes, Contraception 57:117-123 (1998).

Teng, C-Fos Protein Expression in Apoptotic Rat Spermatocytes Induced by Gossypol, Contraception 57:281-286 (1998).

Thoenes et al., Cytotoxic Effects of Adriamycin, Bleomycin, Gossupol and Hydroxyanisol to Cultured Human Malignant Melonoma Cells, Journal of Cancer Research and Clinical Onocology, 113:D-THER:12,S46 (1987).

Thomas et al., Effects of Gossylpol on the Cell Cycle Phases in T-47 Human Breat Cancer Cells, Anticancer Research 11:1469-1476 (1991).

D.K. Trask et al., Laryngoscope, 112:638-644 (2002).

Troll et al., Free Oxygen Radicals: Necessary Contributors to Tumor Promotion and Cocarcinogenesis, Proceedings of the 14th International Symposium of The Princess Takamatsu Cancer Research Fund, 207-218 (1984).

Tso, Gossypol Inhibits Ehrlich Ascites Tumor Cell Proliferation, Cancer Letters 24:257-261 (1984).

Tuszynski et al., Differential Cytotoxic Effect of Gossypol on Human Melanoma, Colon Carcinoma, and Other Tissue Culture Cell Lines, Cancer Research 44:768-771 (1984).

Vander Jagt et al., Gossypol: Prototype of Inhibitors Targeted to Dinucleotide Folds, Current Medicinal Chemistry 7:479-498 (2000).

Van Poznak et al., Oral Gossypol in the treatment of patients with refractory metastatic breast cancer: A phase I/II clinical trial, Breat Cancer Research and Treatment 66:239-248 (2001).

Vlietinck et al., Plant-Derived Leading Compounds for Chemotherapy of Human Immunodeficiency Virus (HIV) Injection, PlantaMedica 64:97-109 (1998).

Wang et al., Effect of Gossypol on DNA Synthesis and Cell Cycle Progression of Mammalian Cells in Vitro, Cancer Research 44:35-38 (1984).

Wang et al., Cytotoxic effect of gossypol on olonn carcinoma cells, Life Sciences 67:2663-2671 (2000).

P. Watkins, Pharmacogenetics, 4:171-184 (1994).

Wichmann et al., Inhibiting herpes simplex virus tyupe 2 infection in human epithelial cells by gossypol, a potent spermicidal and contraceptive agent, Am. J. Obstet. Gynecol. 142:593-594 (1982).

Wu et al., Pharmacokinetics of (±)-, and (+)-, and (−)-gossypol in humans and dogs, Clinical Pharmacology & Therapeutics 39:613-618 (1996).

Wu et al., An in Vitro and in Vivo Study of Antitumor Effects of Gossypol on Human SW-13 Andrenocortical Carcinoma, Cancer Research 49:3743-3758 (1989).

Wu et al., In vitro antitumor activity of gossypol alone or in combination with amsacrine, European Journal of Pharmacology 183:230 (1990).

Xueqing et al., Clinical Observation and Experimental Study of Gossypol in Treatment of Dysfunctional Menorrhagia, Endometriosis and Fibromyoma of Uterus, Chinese Journal of Integrated Traditional and Western Medicine 8:197 (1988).

Ye et al., The Modulation of Gap Junctional Communication by Gossypol in Various Mammalian Cell Lines in Vitro, Fundamental And Applied Toxicology 14:817-832 (1990).

Ye et al., Toxicity of a Male Contraceptive, Gossypol, in Mammalian Cell Cultures, In Vitro 19:53-57 (1983).

Yikang et al., Studies on Resolution of Racemic Gossypol, Scientia Sinica 30:297-303 (1987).

Ying et al., Studies on Frequencies of Sister Chromatid Exchange in Peripheral Blood Lymphocytes Before and After Gossypol Treatment, Proc. DAMS and PUMC 1:34-36 (1986).

Youfang et al., Ultrastructural Changes of Smooth Muscle Cells in Leiomyoma and Myometrium of Human Uterus after Gossypol Treatment, ACTA Academiae Medicinae Sinicae, 9:299-301 (1987).

Yu, Probing Into the Mechanism of Action, Metabolism and Toxicity of Gossypol by Studying its (+)- and (−)- Stereoisomers, Journal of Ethnopharmacology 20:65-78 (1987).

Zhang et al., The (-)-enantiomer of gossypol inhibits proliferation of stromal cells derived from human breast adipose tissues by enhancing transforming growth factor $\beta_1$ production, International Journal of Oncology 13:1291-1297 (1998).

* cited by examiner

| # | Structure | Binding IC$_{50}$ μM | # | Structure | Binding IC$_{50}$ μM |
|---|---|---|---|---|---|
| 5 | 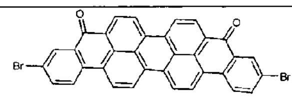 | 7.7 ± 4.5 | 9 | 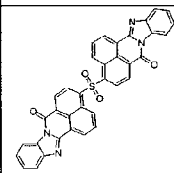 | 14.0 ± 2.8 |
| 6 | 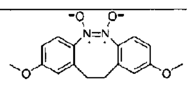 | 10.4 ± 0.3 | 10 | 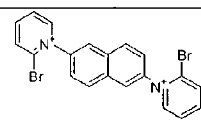 | 11.7 ± 2.4 |
| 7 | 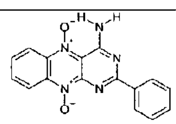 | 1.6 ± 0.1 | 11 | 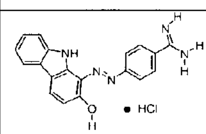 | 5.8 ± 2.2 |
| 8 | 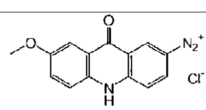 | 10.4 ± 1.2 | | | |

Fig. 5

| # | Structure | Calculated Mass (M) | Observed Mass | # | Structure | Calculated Mass (M) | Observed Mass |
|---|---|---|---|---|---|---|---|
| 5 | 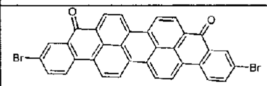 | 611.94 | 613.2 (M+H)⁺ | 9 | 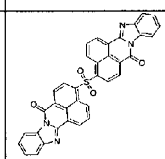 | 602.10 | 1241.8 (M)⁺ or 352.3 (M)⁻ |
| 6 | 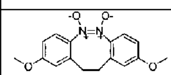 | 300.11 | 300.9 (M+H)⁺ | 10 | 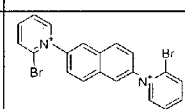 | 597.79 | 538 (M)⁻ |
| 7 | 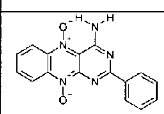 | 305.05 | 305.4 (M)⁻ | 11 | 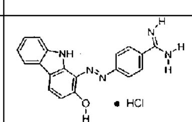 | 365.10 329.10 (-HCl) | 330.1 (M+H)⁺ |
| 8 | 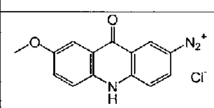 | 258.04 (with Cl⁻) 222.06 (no Cl⁻) | 222.1 (M)⁺ | | | | |

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Gly Phe Leu Gly
1

US 7,354,928 B2

SMALL MOLECULE INHIBITORS TARGETED AT BCL-2

This application claims priority to U.S. Provisional Patent Applications 60/330,865 filed Nov. 1, 2001, and No. 60/363,836, filed Mar. 2, 2002. The disclosures of these applications are specifically incorporated herein in their entireties.

FIELD OF THE INVENTION

The present invention relates to small molecule antagonists of Bcl-2 family proteins such as Bcl-2 and/or Bcl-$X_L$. In particular, the present invention provides non-peptide cell permeable small molecules (e.g., tricyclo-dibenzo-diazocine-dioxides) that bind to a pocket in Bcl-2/Bcl-$X_L$ that block the anti-apoptotic function of these proteins in cancer cells and tumor tissues exhibiting Bcl-2 protein overexpression. In preferred embodiments, the small molecules of the present invention are active at the BH3 binding pocket of Bcl-2 family proteins (e.g., Bcl-2, Bcl-$X_L$, and Mcl-1). The compositions and methods of the present invention are useful therapeutics for cancerous diseases either alone or in combination with chemotherapeutic or other drugs.

BACKGROUND OF THE INVENTION

Multicellular organisms use a process called apoptosis to instruct damaged or unnecessary cells to destroy themselves for the good of the organism. Control of the apoptotic process is very important to the normal development of the organism. For example, development of fetal fingers and toes requires the controlled removal, by apoptosis, of excess interconnecting tissues, as does the proper formation of neural synapses within the brain. Similarly, controlled apoptosis is responsible for the sloughing off of the inner lining of the uterus (the endometrium) at the start of menstruation.

Apoptosis not only plays an important role in tissue sculpting during development and normal cellular maintenance, it is also the primary defense against cells that pose a threat to the well being of the organism. In the cell-mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. The CTLs induce apoptosis in each other and even in themselves thus preventing autoimmunity. Defects in this process are associated with a variety of debilitating autoimmune diseases such as lupus erythematosus and rheumatoid arthritis.

Normally, multicellular organisms also use the apoptotic process to instruct cells with damaged nucleic acids (e.g., DNA) to destroy themselves prior to becoming cancerous. However, some cancer-causing viruses prevent infected cells from initiating the apoptotic process. Two human papilloma viruses (HPV) have been implicated in causing cervical cancer by suppressing apoptotic removal of transformed cells by producing a protein (E6) that inactivates the p53 apoptosis promoter. Epstein-Barr virus (EBV), the causative agent of mononucleosis and Burkitt's lymphoma a solid tumor of B lymphocytes, produces a protein similar to Bcl-2 and another that causes infected cells to increase production of Bcl-2. Both of these mechanisms make the Epstein-Barr virus infected cells resistant to apoptosis thus allowing the cancerous cells to proliferate and to spread throughout the organism.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete elevated levels of soluble decoy molecules that bind to FasL, inhibiting it from binding to Fas. CTLs are thus prohibited from destroying these protected cancer cells. Other cancer cells express high levels of FasL, again, avoiding destruction by the CTLs. Still other viruses manipulate the cell's apoptotic machinery without directly resulting in the development of a cancer. For example, destruction of the immune system in individuals infected with the human immunodeficiency virus (HIV) progresses by infected $CD4^+$ T cells (about 1 in 100,000) instructing uninfected $CD4^+$ T cells to undergo apoptosis.

Various degenerative conditions and vascular diseases may also result from faulty regulation of the apoptotic machinery.

It is apparent that the controlled regulation of the apoptotic process and the apoptotic machinery is vital to the survival of multicellular organisms. Typically, the biochemical changes that occur in a cell instructed to undergo apoptosis occur in an orderly procession. However, as shown above, flawed regulation of the apoptotic process and machinery can cause serious deleterious effects and diseases to arise in an organism.

There have been various attempts to control and restore regulation of the apoptotic machinery in aberrant cells (e.g., cancer cells). Generally, these attempts have had limited success as treatments for the underlying diseases characterized by the faulty regulation of the apoptotic machinery for a number of reasons, such as, toxicity, ineffectiveness, high costs, and the like. The art needs improved compositions and methods of regulating apoptosis in subjects afflicted with diseases and conditions characterized by faulty regulation of the apoptotic process.

SUMMARY OF THE INVENTION

The present invention relates to small molecule antagonists of Bcl-2 family proteins such as Bcl-2 and/or Bcl-$X_L$. In particular, the present invention provides non-peptide cell permeable small molecules (e.g., tricyclo-dibenzo-diazocine-dioxides) that bind to a pocket in Bcl-2/Bcl-$X_L$ that block the anti-apoptotic function of these proteins in cancer cells and tumor tissues exhibiting Bcl-2 protein overexpression. In preferred embodiments, the small molecules of the present invention are active at the BH3 binding pocket of Bcl-2 family proteins (e.g., Bcl-2, Bcl-$X_L$, and Mcl-1). The compositions and methods of the present invention are useful therapeutics for cancerous diseases either alone or in combination with chemotherapeutic or other drugs.

Bcl-2 is the founding member of a family of proteins and was first isolated as the product of an oncogene. The Bcl-2 family of proteins now includes both anti-apoptotic molecules such as Bcl-2 and Bcl-$X_L$ and pro-apoptotic molecules such as Bax, Bak, Bid, and Bad. Bcl-2 and Bcl-$X_L$ are important regulators of Bcl-2 family mediated apoptosis.

While the present invention is not limited to any particular mechanism, and indeed and understanding of the mechanisms of the molecules disclosed herein is unnecessary for practicing the invention, the present invention contemplates that the small molecule compounds disclosed herein bind to the BH3 binding site of Bcl-2 family proteins, in particular Bcl-2, Bcl-$X_L$, and Mcl-1. The present invention further contemplates that the compounds of the present invention are effective modulators (e.g., promoters and/or inhibitors) of the activity of Bcl-2 family proteins.

In preferred embodiments, the present invention contemplates that administration of the small molecule compounds disclosed herein provides an effective treatment for neoplastic conditions and other disorders that involve the aberrant hyperproliferation of cells (e.g., tumor cells).

In other preferred embodiments, the present invention provides methods of cancer treatment or prophylaxis that comprise administering to a subject a small molecule compound (or an analogue thereof) in an effective amount to inhibit the anti-apoptotic activity of Bcl-2 and/or Bcl-$X_L$ thus increasing tumor suppression and/or inducing apoptosis.

In some embodiments, the small molecule compounds of the present invention are, or analogues thereof, are administered in conjunction with a tumor cell apoptosis promoting agent (e.g., Geranylgeraniol [3,7,11,15-tetramethyl-2,6,10,14-hexadecatraen-1-ol]). The present invention contemplates that increasing tumor cell apoptosis reestablishes normal apoptotic control associated with basal levels of Bcl-2 and/or Bcl-$X_L$ expression.

The methods of the present invention are particularly well suited for the treatment of a cancers characterized by overexpression of Bcl-2 family proteins, including, but not limited to, Bcl-2 and/or Bcl-$X_L$.

In some embodiments, the compositions and methods of the present invention provide treatments for a number of conditions including, but not limited to, breast cancer; prostate cancer; lung cancer; lymphomas; skin cancer; pancreatic cancer; colon cancer; melanoma; ovarian cancer; brain cancer; head and neck cancer; liver cancer; bladder cancer; non-small lung cancer; cervical carcinoma; leukemia; neuroblastoma and glioblastoma; T and B cell mediated autoimmune diseases; inflammatory diseases; infections; hyperproliferative diseases; AIDS; degenerative conditions, and vascular diseases and the like. In some embodiments, metastatic cancer cells are treated.

In one preferred embodiment, the present invention provides methods of modulating apoptosis in a cell comprising providing: a cell, wherein the cell overexpresses a Bcl-2 family protein; a small molecule compound described in the present invention; and treating the cell with an effective amount of the compound under conditions such that apoptosis in the cell is modulated.

In some embodiments, infections suitable for treatment with the compositions and methods of the present invention include, but are limited to, infections caused by viruses, bacteria, fungi, mycoplasma, and the like. The present invention is not limited, however, to treating of any particular infections or infectious agents.

The methods of the present invention are not limited to particular administration route or to the specifically recited compounds. Indeed, the present invention contemplates the administration of suitable enantiomers, metabolites, derivatives, and pharmaceutically acceptable salts of the present compositions.

In some embodiments, the Bcl-2 family protein modulated by the methods and compositions of the present invention include, but are not limited to, Bcl-2, Bcl-$X_L$, MCl-1, A1/BFL-1, and BOO-DIVA. In still embodiments, the Bcl-2 family proteins have pro-apoptotic activity. In yet other embodiments, the Bcl-2 family proteins have anti-apoptotic activity.

In one preferred embodiment, the present invention provides methods of modulating cell division in a tissue comprising: providing: a tissue, wherein the tissue overexpresses a Bcl-2 protein; a small molecule compound (optionally one or more anticancer agents); and treating the tissue with effective amounts of the small molecule compound under conditions such that cell division is modulated.

The present invention contemplates a number of anticancer agents are suitable for use in the present methods. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons [e.g., IFN-α, etc.] and interleukins [e.g., IL-2, etc.], etc.); adoptive immunotherapy agents; hematopoietic growth factors; agents that induce tumor cell differentiation (e.g., all-trans-retinoic acid, etc.); gene therapy reagents; antisense therapy reagents and nucleotides; tumor vaccines; and inhibitors of angiogenesis, and the like. Numerous other examples of chemotherapeutic compounds and anticancer therapies suitable for co-administration with the disclosed small molecule compounds are known to those skilled in the art.

In preferred embodiments, anticancer agents comprise agents that induce or stimulate apoptosis. Agents that induce apoptosis include, but are not limited to, radiation (e.g., UV); kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal anti-inflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or taxol]; cellular signaling molecules; ceramides and cytokines; and staurosprine, and the like.

Still other methods provide cancer treatments in a subject comprising: administering to a patient having cancer, wherein the cancer is characterized by resistance to cancer therapies (e.g., chemoresistant, radiation resistant, hormone resistant, and the like), an effective amount of a small molecule compound disclosed herein.

Yet other embodiments of the present invention, provide methods of treating cancer in a subject comprising administering to a patient having cancer, wherein the cancer is characterized by overexpression of a Bcl-2 family protein, a dose of a small molecule compound of the present invention (and optionally at least one anticancer agent) sufficient to reduce the overexpression of the protein.

Other embodiments the present invention provide pharmaceutical compositions comprising: a small molecule compounds as disclosed herein; and instructions for administering the small molecule compounds to a subject, the subject characterized by overexpression of a Bcl-2 family protein.

Further embodiments of the present invention provide pharmaceutical compositions comprising: a small molecule-compound; and instructions for administering the small molecule compound to a subject, the subject characterized by resistance to a cancer therapy. In preferred embodiments, the instructions included with these kits meet U.S. Food and Drug Administrations rules, regulations, and suggestions for provision of therapeutic compounds.

In yet another embodiment, the present invention provides methods of screening a small molecule compound and a test compound comprising: providing: a small molecule compound; a test compound; a first group of cells; and contacting the first group of cells with the small molecule compound and the test compound; and observing the effects of contacting the first group of cells with the small molecule compound and the test compound. In some of these embodiments, the present invention further provides the additional step of comparing the effects observed in the first cells against a second group of the cells contacted with the small molecule compound alone, or with the test compound alone. Effects that may be observed include, but are not limited to, changes in cell proliferation, changes in apoptotic status, and changes in the expression of Bcl-2 family proteins (e.g., Bcl-2 and/or Bcl-$X_L$), and the like. In still other embodiments, the present invention further contemplates additional methods for selling test compounds screened/identified by the above methods. In some of these embodiments, test compounds offered for sale by a third party come in one or more forms (e.g., a kit, including, instructions for administering the test compound to a patient).

Specific and preferred values provided herein for radicals, substituents, and ranges are for illustration only; they do not exclude other defined values or other values within defined ranges for the radicals and substituents.

The groups ($C_1$-$C_6$) alkyl, ($C_2$-$C_6$) alkenyl, ($C_1$-$C_6$) alkoxy, and ($C_1$-$C_6$) dialkylamino, correspond in formula II, for example, Compound 6 to carbon, oxygen and nitro atoms or groups substituted with hydrocarbon substituents which can be either branched or straight chain carbon groups containing the number of carbon atoms designated in parentheses. All terms, for example, alkoxy, hydroxy, phenyl, fluorine, chlorine, bromine, iodine are terms that would be readily recognized.

Those skilled in the art appreciate that compounds of the present invention having one or more chiral center(s) may exist in and be isolated in optically active racemic forms. Some compounds may exhibit polymorphism. It is understood that the present invention encompasses any racemic, optically active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine the ability of a compound to promote apoptosis using the tests described herein, or using other tests which are well known in the art.

In one embodiment, the present invention provides seven structurally distinct formulas, for example, formulas I to VII (See, Table 1), of active compounds and methods of using these compounds in therapeutically effective amounts for modulating (e.g., promoting) apoptosis and/or treating cancer in a subject in need thereof.

In another embodiment, the present invention provides methods for modulating (e.g., promoting) apoptosis and/or treating cancer comprising administering to a subject in need thereof a therapeutically effective amount the compound of Formula I:

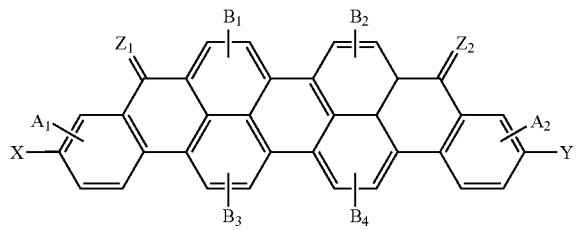

wherein X and Y are each independently selected from hydrogen, fluorine, chlorine, bromine and iodine; $Z_1$ and $Z_2$ are each independently O or S; $A_1$ and $A_2$ are each independently 1 to 3 substituents and selected from hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, $NH((C_1$-$C_6)$alkyl), $N((C_1$-$C_6)$alkyl)$_2$, $NO_2$, CN, COOH, COO($C_1$-$C_6$)alkyl, $CONH_2$, CONH($C_1$-$C_6$)alkyl, CON(($C_1$-$C_6$)alkyl)$_2$, O—($C_1$-$C_6$)alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH(($C_1$-$C_6$)alkyl), N(($C_1$-$C_6$)alkyl)$_2$, NH—CO—$CH_3$ or N(COOCH$_2$Ph)$_2$), $SO_2$—$NH_2$, $SO_2$NH($C_1$-$C_6$)alkyl, $SO_2$N(($C_1$-$C_6$)alkyl)$_2$, S—($C_1$-$C_6$)alkyl, S—($CH_2$)$_n$-phenyl, SO—($C_1$-$C_6$)alkyl, SO—($CH_2$)$_n$-phenyl, $SO_2$—($C_1$-$C_6$)-alkyl, $SO_2$—($CH_2$)$_n$-phenyl (where n is 0-6 and the phenyl radical may be substituted up to two times by F, Cl, Br, I, OH, $CF_3$, $NO_2$, CN, $OCF_3$, O—($C_1$-$C_6$)-alkyl, ($C_1$-$C_6$)-alkyl, $NH_2$, NH(($C_1$-$C_6$)alkyl), N(($C_1$-$C_6$)alkyl)$_2$), NH($C_1$-$C_7$)-acyl, phenyl, biphenylyl, O—($CH_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); $B_1$, $B_2$, $B_3$ and $B_4$ are each independently 1 to 2 substituents and selected from hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, NH(($C_1$-$C_6$)alkyl), N(($C_1$-$C_6$)alkyl)$_2$, $NO_2$, CN, COOH, COO($C_1$-$C_6$)alkyl, $CONH_2$, CONH($C_1$-$C_6$)alkyl, CON(($C_1$-$C_6$)alkyl)$_2$, O—($C_1$-$C_6$)alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH(($C_1$-$C_6$)alkyl), N(($C_1$-$C_6$)alkyl)$_2$, NH—CO—$CH_3$ or N(COOCH$_2$Ph)$_2$), $SO_2$—$NH_2$, $SO_2$NH($C_1$-$C_6$)alkyl, $SO_2$N(($C_1$-$C_6$)alkyl)$_2$, S—($C_1$-$C_6$) alkyl, S—($CH_2$)$_n$-phenyl, SO—($C_1$-$C_6$)-alkyl, SO—($CH_2$)$_n$-phenyl, $SO_2$—($C_1$-$C_6$)-alkyl, $SO_2$—($CH_2$)$_n$-phenyl (where n is 0-6 and the phenyl radical may be substituted up to two times by F, Cl, Br, I, OH, $CF_3$, $NO_2$, CN, $OCF_3$, O—($C_1$-$C_6$)-alkyl, ($C_1$-$C_6$)-alkyl, $NH_2$, NH(($C_1$-$C_6$)alkyl), N(($C_1$-$C_6$)alkyl)$_2$), NH($C_1$-$C_7$)-acyl, phenyl, biphenylyl, O—($CH_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, COOH, COO—($C_1$-$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); and pharmaceutically acceptable salts and deritives thereof.

In another embodiment, the present invention provides methods for modulating (e.g., promoting) apoptosis and/or treating cancer comprising administering to a subject in need thereof a therapeutically effective amount the compound of Formula II:

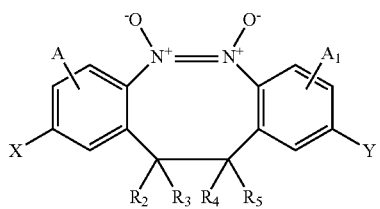

wherein X and Y are each independently hydrogen, OR or $OR_1$; wherein R and $R_1$ are each independently hydrogen, ($C_1$-$C_6$)-alkyl, ($C_2$-$C_6$)-alkenyl, ($C_3$-$C_8$)-cycloalkyl, phenyl or trifluoromethyl; wherein $R_2$, $R_3$, $R_4$ and $R_5$ are each independently hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, $NH((C_1$-$C_6)$alkyl), $N((C_1$-$C_6)$alkyl$)_2$, $NO_2$, CN, COOH, COO($C_1$-$C_6$)alkyl, $CONH_2$, $CONH(C_1$-$C_6)$alkyl, $CON((C_1$-$C_6)$alkyl$)_2$, O—($C_1$-$C_6$)alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, $NH((C_1$-$C_6)$alkyl), $N((C_1$-$C_6)$alkyl$)_2$, NH—CO—$CH_3$ or $N(COOCH_2Ph)_2$), $SO_2$—$NH_2$, $SO_2NH(C_1$-$C_6)$alkyl, $SO_2N((C_1$-$C_6)$alkyl$)_2$, S—($C_1$-$C_6$)alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl (where n is 0-6 and the phenyl radical may be substituted up to two times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH((C_1$-$C_6)$alkyl), $N((C_1$-$C_6)$alkyl$)_2$), $NH(C_1$-$C_7)$-acyl, phenyl, biphenylyl, O—$(CH_2)_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, COOH, COO—($C_1$-$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); A and $A_1$ are each independently 1 to 3 substituents selected from hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, $NH((C_1$-$C_6)$alkyl), $N((C_1$-$C_6)$alkyl$)_2$, $NO_2$, CN, COOH, COO($C_1$-$C_6$)alkyl, $CONH_2$, $CONH(C_1$-$C_6)$alkyl, $CON((C_1$-$C_6)$alkyl$)_2$, O—($C_1$-$C_6$)alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, $NH((C_1$-$C_6)$alkyl), $N((C_1$-$C_6)$alkyl$)_2$, NH—CO—$CH_3$ or $N(COOCH_2Ph)_2$), $SO_2$—$NH_2$, $SO_2NH(C_1$-$C_6)$alkyl, $SO_2N((C_1$-$C_6)$alkyl$)_2$, S—($C_1$-$C_6$)alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl (where n is 0-6 and the phenyl radical may be substituted up to two times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH((C_1$-$C_6)$alkyl), $N((C_1$-$C_6)$alkyl$)_2$), $NH(C_1$-$C_7)$-acyl, phenyl, biphenylyl, O—$(CH_2)_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH((C_1$-$C_6)$-alkyl), $N((C_1$-$C_6)$-alkyl$)_2$, $SO_2$—$CH_3$, COOH, COO—($C_1$-$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); and pharmaceutically acceptable salts and deritives thereof.

The compound shown in Formula II is believed to exist in equilibrum as the following structures:

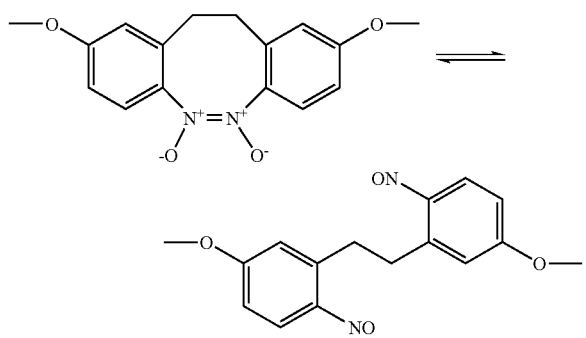

In another embodiment, the present invention provides methods for modulating (e.g., promoting) apoptosis and/or treating cancer comprising administering to a subject in need thereof a therapeutically effective amount the compound of Formula III:

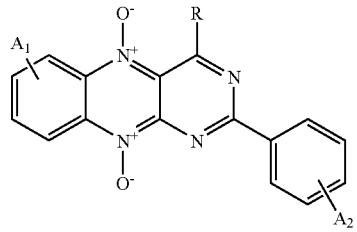

wherein R is selected from $NH_2$, $NH((C_1$-$C_6)$alkyl) and $N((C_1$-$C_6)$alkyl$)_2$; $A_1$ is 1 to 4 substituents selected from hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, $NH((C_1$-$C_6)$alkyl), $N((C_1$-$C_6)$alkyl$)_2$, $NO_2$, CN, COOH, COO($C_1$-$C_6$)alkyl, $CONH_2$, $CONH(C_1$-$C_6)$alkyl, $CON((C_1$-$C_6)$alkyl$)_2$, O—($C_1$-$C_6$) alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, $NH((C_1$-$C_6)$alkyl), $N((C_1$-

$C_6$)alkyl)$_2$, NH—CO—CH$_3$ or N(COOCH$_2$Ph)$_2$), SO$_2$—NH$_2$, SO$_2$NH(C$_1$-C$_6$)alkyl, SO$_2$N((C$_1$-C$_6$)alkyl)$_2$, S—(C$_1$-C$_6$)alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl (where n is 0-6 and the phenyl radical may be substituted up to two times by F, Cl, Br, T, OH, CF$_3$, NO$_2$, CN, OCF$_3$, O—(C$_1$-C$_6$)-alkyl, (C$_1$-C$_6$)-alkyl, NH$_2$, NH((C$_1$-C$_6$)alkyl), N((C$_1$-C$_6$)alkyl)$_2$), NH(C$_1$-C$_7$)-acyl, phenyl, biphenylyl, O—(CH$_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); A$_2$ is 1 to 5 substituents selected from hydrogen, hydroxy, branched or straight chain (C$_1$-C$_6$)-alkyl, branched or straight chain (C$_2$-C$_6$)-alkenyl, (C$_3$-C$_8$)-cycloalkyl, phenyl, aryl, (C$_1$-C$_6$)-alkoxy, CZ$_3$ (wherein Z is selected from F, Cl, Br and I), NH$_2$, NH((C$_1$-C$_6$)alkyl), N((C$_1$-C$_6$)alkyl)$_2$, NO$_2$, CN, COOH, COO(C$_1$-C$_6$)alkyl, CONH$_2$, CONH(C$_1$-C$_6$)alkyl, CON((C$_1$-C$_6$)alkyl)$_2$, O—(C$_1$-C$_6$)alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH((C$_1$-C$_6$)alkyl), N((C$_1$-C$_6$)alkyl)$_2$, NH—CO—CH$_3$ or N(COOCH$_2$Ph)$_2$), SO$_2$—NH$_2$, SO$_2$NH(C$_1$-C$_6$)alkyl, SO$_2$N((C$_1$-C$_6$)alkyl)$_2$, S—(C$_1$-C$_6$)alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl (where n is 0-6 and the phenyl radical may be substituted up to two times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH((C$_1$-C$_6$)alkyl), N((C$_1$-C$_6$)alkyl)$_2$), NH(C$_1$-C$_7$)-acyl, phenyl, biphenylyl, O—(CH$_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); or a pharmaceutically acceptable salt thereof.

In another embodiment, the present invention provides methods for modulating (e.g., promoting) apoptosis and/or treating cancer comprising administering to a subject in need thereof a therapeutically effective amount the compound of Formula IV:

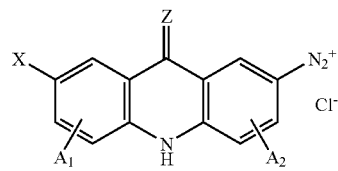

wherein, Z is O or S; X is selected from hydrogen and OR, wherein R is selected from hydrogen, (C$_1$-C$_6$)-alkyl, (C$_2$-C$_6$)-alkenyl, (C$_3$-C$_8$)-cycloalkyl, phenyl and trifluoromethyl; A$_1$ and A$_2$ are each independently 1 to 3 substituents selected from hydrogen, hydroxy, branched or straight chain (C$_1$-C$_6$)-alkyl, branched or straight chain (C$_2$-C$_6$)-alkenyl, (C$_3$-C$_8$)-cycloalkyl, phenyl, aryl, (C$_1$-C$_6$)-alkoxy, CZ$_3$ (wherein Z is selected from F, Cl, Br and I), NH$_2$, NH((C$_1$-C$_6$)alkyl), N((C$_1$-C$_6$)alkyl)$_2$, NO$_2$, CN, COOH, COO(C$_1$-C$_6$)alkyl, CONH$_2$, CONH(C$_1$-C$_6$)alkyl, CON((C$_1$-C$_6$)alkyl)$_2$, O—(C$_1$-C$_6$)alkyl (where one, more than one or all hydrogens) in the alkyl radicals may be replaced by fluorine, or one hydrogen may be replaced by OH, OC(O)CH$_3$, OC(O)H, O—CH$_2$—Ph, NH$_2$, NH((C$_1$-C$_6$)alkyl), N((C$_1$-C$_6$)alkyl)$_2$, NH—CO—CH$_3$ or N(COOCH$_2$Ph)$_2$), SO$_2$—NH$_2$, SO$_2$NH(C$_1$-C$_6$)alkyl, SO$_2$N((C$_1$-C$_6$)alkyl)$_2$, S—(C$_1$-C$_6$) alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl (where n is 0-6 and the phenyl radical may be substituted up to two times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH((C$_1$-C$_6$)alkyl), N((C$_1$-C$_6$)alkyl)$_2$), NH(C$_1$-C$_7$)-acyl, phenyl, biphenylyl, O—(CH$_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); and pharmaceutically acceptable salts and deritives thereof.

Another embodiment of the present invention provides methods for modulating (e.g., promoting) apoptosis and/or treating cancer comprising administering to a subject in need thereof a therapeutically effective amount the compound of Formula V:

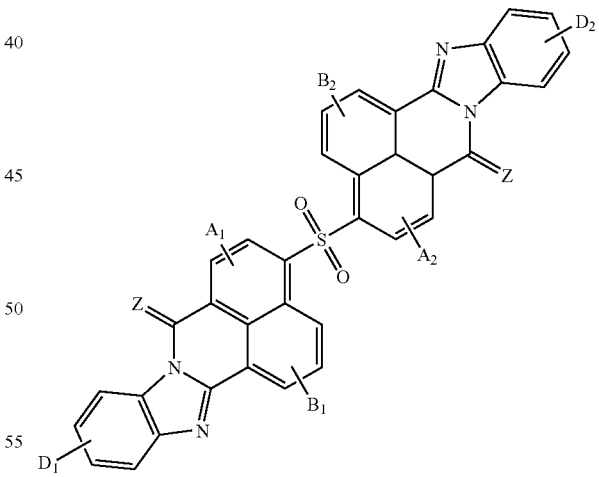

wherein Z is O or S; A$_1$ and A$_2$ are each independently 1 or 2 substituents selected from hydrogen, hydroxy, branched or straight chain (C$_1$-C$_6$)-alkyl, branched or straight chain (C$_2$-C$_6$)-alkenyl, (C$_3$-C$_8$)-cycloalkyl, phenyl, aryl, (C$_1$-C$_6$)-alkoxy, CZ$_3$ (wherein Z is selected from F, Cl, Br and I), NH$_2$, NH((C$_1$-C$_6$)alkyl), N((C$_1$-C$_6$)alkyl)$_2$, NO$_2$, CN, COOH, COO(C$_1$-C$_6$)alkyl, CONH$_2$, CONH(C$_1$-C$_6$)alkyl, CON((C$_1$-C$_6$)alkyl)$_2$, O—(C$_1$-C$_6$(where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH((C$_1$-C$_6$)alkyl), N((C$_1$-C$_6$)alkyl)$_2$, NH—CO—CH$_3$ or N(COOCH$_2$Ph)$_2$), SO$_2$—NH$_2$, SO$_2$NH(C$_1$-C$_6$)alkyl, SO$_2$N((C$_1$-C$_6$)alkyl)$_2$, S—(C$_1$-C$_6$)alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl (where n is 0-6 and the phenyl radical may be substituted up to two times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH((C$_1$-C$_6$)alkyl), N((C$_1$-C$_6$)alkyl)$_2$), NH(C$_1$-C$_7$)-acyl, phenyl, biphenylyl, O—(CH$_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); B$_1$ and B$_2$ are each independently 1 to 3 substituents selected from hydrogen, hydroxy, branched or straight chain (C$_1$-C$_6$)-alkyl, branched or straight chain (C$_2$-C$_6$)-alkenyl, (C$_3$-C$_8$)-cycloalkyl, phenyl, aryl, (C$_1$-C$_6$)-alkoxy, CZ$_3$ (wherein Z is selected from F, Cl, Br and I), NH$_2$, NH((C$_1$-C$_6$)alkyl), N((C$_1$-C$_6$)alkyl)$_2$, NO$_2$, CN, COOH, COO(C$_1$-C$_6$)alkyl, CONH$_2$, CONH(C$_1$-C$_6$)alkyl, CON((C$_1$-C$_6$)alkyl)$_2$, O—(C$_1$-C$_6$)alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH((C$_1$-C$_6$)alkyl), N((C$_1$-C$_6$)alkyl)$_2$, NH—CO—CH$_3$ or N(COOCH$_2$Ph)$_2$), SO$_2$—NH$_2$, SO$_2$NH(C$_1$-C$_6$)alkyl, SO$_2$N((C$_1$-C$_6$)alkyl)$_2$, S—(C$_1$-C$_6$)alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl (where n is 0-6 and the phenyl radical may be substituted up to two times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH((C$_1$-C$_6$)alkyl), N((C$_1$-C$_6$)alkyl)$_2$), NH(C$_1$-C$_7$)-acyl, phenyl, biphenylyl, O—(CH$_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position$_1$ or $_2$ by methyl or benzyl); D$_1$ and D$_2$ are each independently 1 to 4 substituents selected from hydrogen, hydroxy, branched or straight chain (C$_1$-C$_6$)-alkyl, branched or straight chain (C$_2$-C$_6$)-alkenyl, (C$_3$-C$_8$)-cycloalkyl, phenyl, aryl, (C$_1$-C$_6$)-alkoxy, CZ$_3$ (wherein Z is selected from F, Cl, Br and I), NH$_2$, NH((C$_1$-C$_6$)alkyl), N((C$_1$-C$_6$)alkyl)$_2$, NO$_2$, CN, COOH, COO(C$_1$-C$_6$)alkyl, CONH$_2$, CONH(C$_1$-C$_6$)alkyl, CON((C$_1$-C$_6$)alkyl)$_2$, O—(C$_1$-C$_6$)alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH((C$_1$-C$_6$)alkyl), N((C$_1$-C$_6$)alkyl)$_2$, NH—CO—CH$_3$ or N(COOCH$_2$Ph)$_2$), SO$_2$—NH$_2$, SO$_2$NH(C$_1$-C$_6$)alkyl, SO$_2$N((C$_1$-C$_6$)alkyl)$_2$, S—(C$_1$-C$_6$)alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl (where n is 0-6 and the phenyl radical may be substituted up to two times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH((C$_1$-C$_6$)alkyl), N((C$_1$-C$_6$)alkyl)$_2$), NH(C$_1$-C$_7$)-acyl, phenyl, biphenylyl, O—(CH$_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); and pharmaceutically acceptable salts and deritives thereof.

In still another embodiment, the present invention provides methods for modulating (e.g., promoting) apoptosis and/or treating cancer comprising administering to a subject in need thereof a therapeutically effective amount the compound of Formula VI:

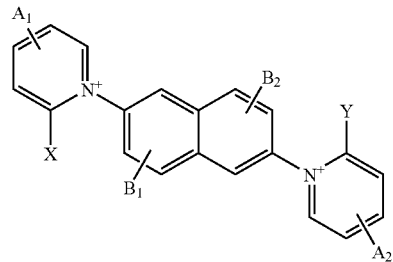

wherein X and Y are each independently selected from hydrogen, fluorine, chlorine, bromine and iodine; A$_1$ and A$_2$ are each independently 1 to 3 substituents selected from hydrogen, hydroxy, branched or straight chain (C$_1$-C$_6$)-alkyl, branched or straight chain (C$_2$-C$_6$)-alkenyl, (C$_3$-C$_8$)-cycloalkyl, phenyl, aryl, (C$_1$-C$_6$)-alkoxy, CZ$_3$ (wherein Z is selected from F, Cl, Br and I), NH$_2$, NH((C$_1$-C$_6$)alkyl), N((C$_1$-C$_6$)alkyl)$_2$, NO$_2$, CN, COOH, COO(C$_1$-C$_6$)alkyl, CONH$_2$, CONH(C$_1$-C$_6$)alkyl, CON((C$_1$-C$_6$)alkyl)$_2$, O—(C$_1$-C$_6$)alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH((C$_1$-C$_6$)alkyl), N((C$_1$-C$_6$)alkyl)$_2$, NH—CO—CH$_3$ or N(COOCH$_2$Ph)$_2$), SO$_2$—NH$_2$, SO$_2$NH(C$_1$-C$_6$)alkyl, SO$_2$N((C$_1$-C$_6$)alkyl)$_2$, S—(C$_1$-C$_6$)alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl (where n is 0-6 and the phenyl radical may be substituted up to two times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH((C$_1$-C$_6$)alkyl), N((C$_1$-C$_6$)alkyl)$_2$), NH(C$_1$-C$_7$)-acyl, phenyl, biphenylyl, O—(CH$_2$)$_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); B$_1$ and B$_2$ are each independently 1 to 3 substituents selected from hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, $NH((C_1$-$C_6)$alkyl), $N((C_1$-$C_6)$alkyl)$_2$, $NO_2$, CN, COOH, COO($C_1$-$C_6$)alkyl, $CONH_2$, $CONH(C_1$-$C_6)$alkyl, $CON((C_1$-$C_6)$alkyl)$_2$, O—($C_1$-$C_6$)alkyl (where one, more than one or all hydrogen(s) in the alkyl radicals may be replaced by fluorine, or one hydrogen may be replaced by OH, $OC(O)CH_3$, $OC(O)H$, O—$CH_2$—Ph, $NH_2$, $NH((C_1$-$C_6)$alkyl), $N((C_1$-$C_6)$alkyl)$_2$, NH—CO—$CH_3$ or $N(COOCH_2Ph)_2$), $SO_2$—$NH_2$, $SO_2NH(C_1$-$C_6)$alkyl, $SO_2N((C_1$-$C_6)$alkyl)$_2$, S—($C_1$-$C_6$)alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl (where n is 0-6 and the phenyl radical may be substituted up to two times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH((C_1$-$C_6)$alkyl), $N((C_1$-$C_6)$alkyl)$_2$), $NH(C_1$-$C_7)$-acyl, phenyl, biphenylyl, O—$(CH_2)_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); and pharmaceutically acceptable salts and deritives thereof.

In yet another embodiment, the present invention provides methods for modulating (e.g., promoting) apoptosis and/or treating cancer comprising administering to a subject in need thereof a therapeutically effective amount the compound of Formula VII:

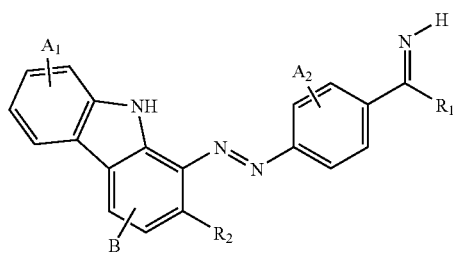

wherein $R_1$ and $R_2$ are each independently hydrogen, $OR_3$ or $OR_4$, $NH_2$, $NH((C_1$-$C_6)$alkyl) or $N((C_1$-$C_6)$alkyl)$_2$; wherein $R_3$ and $R_4$ are each independently hydrogen, ($C_1$-$C_6$)-alkyl, ($C_2$-$C_6$)-alkenyl, ($C_3$-$C_8$)-cycloalkyl, phenyl or trifluoromethyl; $A_1$ and $A_2$ are each independetly 1 to 4 substituents selected from hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, $NH((C_1$-$C_6)$alkyl), $N((C_1$-$C_6)$alkyl)$_2$, $NO_2$, CN, COOH, COO($C_1$-$C_6$)alkyl, $CONH_2$, $CONH(C_1$-$C_6)$alkyl, $CON((C_1$-$C_6)$alkyl)$_2$, O—($C_1$-$C_6$) alkyl (where one, more than one or all hydrogen(s) in the alkyl radicals may be replaced by fluorine, or one hydrogen may be replaced by OH, $OC(O)CH_3$, $OC(O)H$, O—$CH_2$—Ph, $NH_2$, $NH((C_1$-$C_6)$alkyl), $N((C_1$-$C_6)$alkyl)$_2$, NH—CO—$CH_3$ or $N(COOCH_2Ph)_2$), $SO_2$—$NH_2$, $SO_2NH(C_1$-$C_6)$alkyl, $SO_2N((C_1$-$C_6)$alkyl)$_2$, S—($C_1$-$C_6$)alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl (where n is 0-6 and the phenyl radical may be substituted up to two times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH((C_1$-$C_6)$alkyl), $N((C_1$-$C_6)$alkyl)$_2$), $NH(C_1$-$C_7)$-acyl, phenyl, biphenylyl, O—$(CH_2)_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); B is 1 or 2 substituents selected from hydrogen, hydroxy, branched or straight chain ($C_1$-$C_6$)-alkyl, branched or straight chain ($C_2$-$C_6$)-alkenyl, ($C_3$-$C_8$)-cycloalkyl, phenyl, aryl, ($C_1$-$C_6$)-alkoxy, $CZ_3$ (wherein Z is selected from F, Cl, Br and I), $NH_2$, $NH((C_1$-$C_6)$alkyl), $N((C_1$-$C_6)$alkyl)$_2$, $NO_2$, CN, COOH, COO($C_1$-$C_6$)alkyl, $CONH_2$, $CONH(C_1$-$C_6)$alkyl, $CON((C_1$-$C_6)$alkyl)$_2$, O—($C_1$-$C_6$)alkyl (where one, more than one or all hydrogen(s) in the alkyl radicals may be replaced by fluorine, or one hydrogen may be replaced by OH, $OC(O)CH_3$, $OC(O)H$, O—$CH_2$—Ph, $NH_2$, $NH((C_1$-$C_6)$alkyl), $N((C_1$-$C_6)$alkyl)$_2$, NH—CO—$CH_3$ or $N(COOCH_2Ph)_2$), $SO_2$—$NH_2$, $SO_2NH(C_1$-$C_6)$alkyl, $SO_2N((C_1$-$C_6)$alkyl)$_2$, S—($C_1$-$C_6$)alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl (where n is 0-6 and the phenyl radical may be substituted up to two times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH((C_1$-$C_6)$alkyl), $N((C_1$-$C_6)$alkyl)$_2$), $NH(C_1$-$C_7)$-acyl, phenyl, biphenylyl, O—$(CH_2)_n$-phenyl (where n is 0-6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position $_1$ or $_2$ by methyl or benzyl); and pharmaceutically acceptable salts and deritives thereof.

Other advantages, benefits, and preferable embodiments of the present invention will be apparent to those skilled in the art.

DESCRIPTION OF THE FIGURES

The following figures form part of the specification and are included to further demonstrate certain aspects and embodiments of the present invention. The present invention is not intended to be limited however to the embodiments specifically recited in these figures.

FIG. 5 shows the results of mass spectral analysis of the active compounds in FIG. 4.

DEFINITIONS

Figure 1:
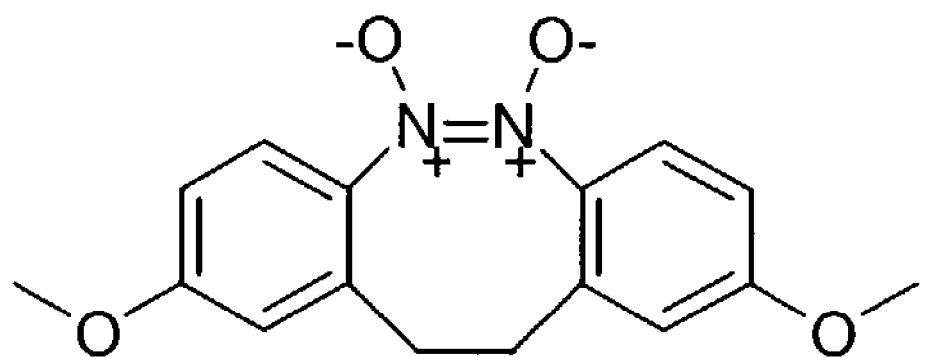
FIG. 1 illustrates the binding of Compound 6 to Bcl-2 protein in vitro as measured by a competitive fluorescence polarization assay. The data points represent the mean of three independent experiments. Bcl-2 used in this assay was a GST-fused soluble protein (Santa Cruz Biotechnology, Inc., CA) and Flu-Bak-BH3 peptide (SEQ ID No: 1, GQVGRQLAIIGDDINR) derived from Bak BH3 domain.

To facilitate an understanding of the present invention, a number of terms and phrases are defined below:

As used herein, the term "cancer" refers to the presence in an organism of cells possessing characteristics typical of cancer-causing cells, for example, uncontrolled proliferation, inhibited apoptosis, immortality, significant metastatic potential, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

The term "tumor," as used herein, refers to all neoplastic cell growth and proliferation, whether malignant or benign, and all precancerous and cancerous cells and tissues.

As used herein, the term "precancerous" refers to cells or tissues having syndromes represented by changes of tissue that may lead to malignancy or cancer. Examples include adenomatous growths in breast, lung tissues, or lesions, whether the precancerous lesions are clinically identifiable or not.

As used herein, the terms "overexpression of Bcl-2," or "overexpression of a Bcl-2 family protein" refer to an elevated level (e.g., aberrant level) of mRNAs encoding Bcl-2 family protein(s), and/or to elevated levels of Bcl-2 family protein(s) in cells or tissues as compared to corresponding nonpathological cells and tissues. Methods for detecting the levels of mRNAs encoding Bcl-2 family proteins, or levels of Bcl-2 family proteins, in a cell or tissue, include, but are not limited to, standard immunohistochemical and/or nucleic acid amplification methods.

As used herein, the terms "anticancer agent," or "conventional anticancer agent" refer to chemotherapeutic compounds, radiation therapies, or surgical interventions, used to treat cancerous cells and tissues.

As used herein the term, "in vitro" refers to an artificial environment and to processes or reactions that occur within an artificial environment. In vitro environments comprise, but are not limited to, test tubes and cell cultures. The term "in vivo" refers to natural environments (e.g., within an animal or within a cell) and to the processes or reactions that occur within natural environments.

As used herein, the term "host cell" refers to any eukaryotic (e.g., animal cells), prokaryotic (e.g., bacteria and archaea cells) whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "subject" refers to organisms treated with the compositions and methods of the present invention. Such organisms include, but are not limited to, humans. In the context of the invention, the term "subject" generally refers to an individual receiving treatment (e.g., administration of Bcl-2 inhibiting compound(s), and optionally one or more anticancer agents) for a disease characterized by overexpression of Bcl-2 family proteins (e.g., Bcl-2, Bcl-$X_L$, Mcl-1, A-1(Bfl-1), and Boo).

The term "diagnosed," as used herein, refers to the recognition of a disease by its signs and symptoms (e.g., resistance to conventional cancer therapies), or genetic analysis, pathological analysis, histological analysis, and the like.

As used herein, the term "competes for binding" refers to a first molecule (e.g., a Bcl-2 inhibitor) that binds to the same substrate (e.g., Bcl-2 and/or Bcl-$X_L$) as does a second molecule (e.g., a pro-apoptotic Bcl-2 family protein, such as, Bax, Bak, Bid, and Bad, etc.). The efficiency (e.g., kinetics or thermodynamics) of binding by the first molecule may be the same as, greater than, or less than, the efficiency of the substrate binding to the second molecule. For example, the equilibrium binding constant ($K_D$) for binding to the substrate may be different for the two molecules.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. For example, once introduced into an embryo, this transcribed strand combines with natural mRNA produced by the embryo to form duplexes. These duplexes then block either the further transcription of the mRNA or its translation. Mutant phenotypes are generated in this manner. The term "antisense strand" refers to a nucleic acid strand that is complementary to the "sense" strand. The designation (−) (i.e., "negative") is sometimes used in reference to the antisense strand, with the designation (+) sometimes used in reference to the sense (i.e., "positive") strand. Regions of a nucleic acid sequences that are accessible to antisense molecules can be determined using available computer analysis methods.

The present invention uses the term "sample," in its broadest sense. A sample suspected of indicating a condition characterized by the overexpression of a Bcl-2 family protein may comprise a cell, tissue, fluid, chromosomes isolated from a cell (e.g., a spread of metaphase chromosomes), genomic DNA (in solution or bound to a solid support such as for Southern blot analysis), RNA (in solution or bound to a solid support such as for Northern blot analysis), or cDNA (in solution or bound to a solid support) and the like. A sample suspected of containing a protein may comprise a cell, a portion of a tissue, or an extract containing one or more proteins and the like.

As used herein, the term "purified" or "to purify" refers, to the removal of undesired components from a sample. As used herein, the term "substantially purified" refers to molecules that are removed from their natural environment, isolated, or separated, and are at least 60% free, preferably 75% free, and most preferably 90% free from other components with which they are naturally associated.

As used herein, the term "organism" is used to refer to any species or type of animal, bacteria, archaea, fungi, protozoans, mycoplasma, and parasitic organisms. As used herein, the term "fungi" is used in reference to eukaryotic organisms such as the molds and yeasts, including dimorphic fungi.

As used herein, the term "pathogen" refers an organism or biological agent (e.g., virus, prions, and the like) that causes a disease state (e.g., infection, cancer, etc.) in another organism. Pathogens include, but are not limited to, viruses, bacteria, archaea, fungi, protozoans, mycoplasma, and parasitic organisms. As used herein, the term "fungi" is used in reference to eukaryotic organisms such as the molds and yeasts, including dimorphic fungi.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

The terms "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process well known in the art. (See e.g., Finegold and Martin, Diagnostic Microbiology, 6th Ed., CV Mosby St. Louis, pp 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "instructions for administering said compound to a subject" includes instructions for using the compositions contained in the kit for the treatment of conditions characterized by the overexpression of a Bcl-2 family protein in a cell or tissue.

The term also refers to instructions for using the compositions contained in the kit to treat cancers characterized as being resistant to at least one conventional anticancer therapy (e.g., chemotherapy). In some embodiments, the instructions further comprise a statement of the recommended or usual dosages of the compositions contained within the kit pursuant to 21 C.F.R. §201 et seq. Additional information concerning labeling and instruction requirements applicable to the methods and compositions of the present are available at the Internet web page of the U.S. FDA.

The term "test compound" refers to any chemical entity, pharmaceutical, drug, and to the like, that can be used to treat or prevent a disease, illness, sickness, or disorder of bodily function, or otherwise alter the physiological or cellular status of a sample (e.g., the level of Bcl-2 family proteins in a cell). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are anticancer agents. In particularly, preferred embodiments, "test compounds" are anticancer agents that induce apoptosis in cells.

As used herein, the term "third party" refers to any entity engaged in selling, warehousing, distributing, or offering for sale a test compound contemplated for co-administered with a gossypol compound for treating conditions characterized by the overexpression of the Bcl-2 family proteins.

As used herein, the term "modulate" refers to the activity of a compound (e.g., gossypol compound) to affect (e.g., to promote or retard) an aspect of the cellular function, including, but not limited to, cell growth, proliferation, apoptosis, and the like.

GENERAL DESCRIPTION OF THE INVENTION

Apoptosis, or programmed cell death is important for normal development, host defense and suppression of oncogenesis and faulty regulation of apoptosis has been implicated in cancer and many other human diseases. Bcl-2 was originally identified at the chromosomal breakpoint of t(14; 18)-bearing B-cell lymphomas and belongs to a growing family of proteins which regulates apoptosis. (See, J. C. Reed, J. Cell. Biol., 124:1-6 [1994]; J. C. Reed, Nature, 387:773-776 [1997]; Hawkins et al., Immunological Reviews, 142:127-139 [1994]; and Minn et al., Advances in Immunology, 70,:245-279 [1998]). In cancerous B cells, the portion of chromosome 18 containing the bcl-2 locus undergoes a reciprocal translocation with the portion of chromosome 14 containing the antibody heavy chains. This t(14; 18) translocation places the bcl-2 gene close to the heavy chain gene enhancer. The product of the Bcl-2 gene, Bcl-2 protein, is an integral membrane protein found in the membranes of the endoplasmic reticulum (ER), nuclear envelope, and the outer membrane of mitochondria.

The Bcl-2 family of proteins includes both anti-apoptotic molecules, for example, Bcl-2 and Bcl-$X_L$ and pro-apoptotic molecules, for example, Bax, Bak, Bid and Bad. These molecules play an important role in regulating apoptosis. (See, Chao et al., Annul. Rev. Immunol., 16:395-419 [1998]; Grosset al., Genes & Develop., 13:1899-1911 [1999]; Hawkins et al., Semin. Immunol., 9:25-33 [1997]; J. C. Reed, Oncogene, 18:3225-3236 [1998]; Park et al., J. Cell. Biochem., 60:12-17 [1996]; J. C. Reed, J. Cell. Biol., 124:1-6 [1994]; J. C. Reed, Nature, 387:773-776 [1997]; J. C. Reed et al., J. Cell. Biochem., 60:23-32 [1996]; Adams et al., Science, 281:1322-1326 [1998]; Hawkins et al., Immunol. Rev., 142:127-139 [1994]).

Although an understanding of the mechanism is not necessary to practice the present invention and the present invention is not so limited, it is contemplated that anti-apoptotic proteins Bcl-2 and Bcl-$X_L$ suppress apoptosis by forming heterodimers with pro-apoptotic Bcl-2 family members such as Bak, Bad, Bax, Mtd (Bok), Bim, Hrk (DP5), Blk, Bnip3, Bnip3L, and Diva. Additional anti-apoptotic members (or related proteins) of the Bcl-2 family are thought to include, but are not limited to, Mcl-1, A-1 (Bfl-1), Boo, and Bcl-W.

In some embodiments, the present invention provides BH3 domain-containing proteins as targets for inhibition. It should be understood that where the specification refers to Bcl-2 families of proteins, the same disclosure pertains to BH3 domain-containing proteins. Thus, in some embodiments, the present invention provides compositions and methods for the regulation of biological conditions related to the aberrant expression of BH3 domain-containing proteins. Likewise, in some other embodiments, the present invention provides method and compositions for screening agents and compounds that modulate (e.g., inhibit or promote) the aberrant expression of BH3 domain-containing proteins.

Bcl-2 and Bcl-$X_L$ are highly homologous proteins. Many forms of human cancers (e.g., myeloid leukemia and breast cancer) overexpress Bcl-2, and/or Bcl-$X_L$. Both Bcl-2 and Bcl-$X_L$ have been found to be overexpressed in human breast cancers. In particular, Bcl-2 is found to be overexpressed in 60-80% of human breast cancers. The expression of Bcl-2 is highly correlated with estrogen receptor (ER) positive breast cancer. Bcl-$X_L$ is overexpressed in 40-70% of human breast cancers, 30-60% of prostate cancers, 80% of B-cell lymphomas, 90% of colorectal adenocarcinomas, and many other forms of cancer. Bcl-$X_L$ is mainly found in ER negative breast cancer. The expression of Bcl-$X_L$ is typically correlates with poor prognosis and shortened survival. The expression levels of Bcl-2 proteins also correlate with resistance to a wide spectrum of chemotherapeutic drugs and γ-radiation therapy. (See, J. C. Reed et al., J. Cell. Biochem., 60:23-32 [1996]; J. C. Reed, Adv. Pharmocology, 41:501-553 [1997]; Strasser et al., Biochem. Biophys. Acta, 1333, F151-F189 [1997]; DiPaola et al., Semin. Oncol., 26:112-116 [1999]).

Several lines of evidence indicate that Bcl-2 and Bcl-$X_L$ not only contribute to cancer progression, but also may confer cancer-resistance to apoptosis induced by conventional anti-cancer therapies. High levels of intracellular Bcl-2 expression protect cells (e.g., cancer cells) from destruction by apoptosis. The majority of solid tumors are protected by at least one of the anti-apoptotic Bcl-2 proteins. Most of the available cancer chemotherapeutic agents target cellular DNA integrity or replication, and indirectly trigger apoptosis in tumor cells. Cancers that express high levels of Bcl-2 and/or Bcl-$X_L$, are often resistant to chemotherapeutic agents or radiation therapy.

However, the expression patterns of Bcl-2 and Bcl-$X_L$ are different in some of the cancers that overexpress Bcl-2 family proteins. Several reports suggest that expression of either Bcl-2 or Bcl-$X_L$ proteins is sufficient for cancer cells to show Bcl-2 family mediated resistance to chemotherapy or radiation therapy. (See, J. C. Reed, Pharmacology, 41:501-553 [1997]; J. C. Reed et al., J. Cell Biochem., 6:23-32 [1996[). Additional research suggests that some cancer cells are able to switch from overexpression of Bcl-2 to Bcl-$X_L$. (See, Z. Han et al., Cancer Res., 56:621-628 [1996]). Accordingly, some embodiments of the present invention provide administering a therapeutic amount of one or more Bcl-2 antagonists (e.g., small molecules) to patients having a cancer characterized by overexpression of Bcl-2. Similarly, other embodiments of the present invention provide administering a therapeutic amount of one or more Bcl-$X_L$ antagonists (e.g., small molecules) to patients having a cancer characterized by overexpression of Bcl-$X_L$. In still further embodiments, the present invention provides administering a combination of two or more Bcl-2 family antagonists (e.g., small molecules) to a patient having a cancer characterized by the overexpression of Bcl-2 family proteins. The present invention further contemplates providing compositions and methods comprising one or more antagonists to Bcl-2 family protein(s) (e.g., an anti-apoptotic Bcl-2 family protein) and one or more additional anticancer agents (e.g., taxol, texotere, docetaxel, etc.). In preferred embodiments, the present invention comprises providing subjets anticancer compositions and methods comprising providing therapeutically effective amounts of a small molecule Bcl-2 modulating compound.

Research into the three-dimensional (3D) structures of Bcl-2 and Bcl-$X_L$ showed that both molecules have a hydrophobic binding pocket (called the BH3 binding pocket) that is important to their anti-apoptotic affects. Further research shows that Bak also has a binding pocket (named BH3) that allows the molecule to bind to the BH3 pockets in Bcl-2 and Bcl-$X_L$. In particular, experimental 3D high-resolution structures of Bcl-$X_L$ (S. W. Muchmore et al., Nature, 381: 335-341 [1996]; and M. Aritomi et al, J. Biol. Chem., 272:27886-27892 [1997]) alone and in complex with a Bak BH3 (Bcl-2 homology domain 3) peptide (S. Michael et al., Science, 275:983-986 [1997]) revealed that the BH1, BH2 and BH3 domains of Bcl-$X_L$ form a hydrophobic binding pocket into which Bak BH3 domain binds. Since Bcl-2 and Bcl-$X_L$ share a high degree of homology in their amino acid sequences (45% of identity and 56% of similarity), analysis of the 3D structure of Bcl-2 modeled from the NMR and X-ray structures of its highly homologous protein Bcl-$X_L$ showed that Bcl-2 has a binding pocket similar to that found in Bcl-$X_L$. This binding pocket in Bcl-2 appears to be important for its anti-apoptotic function since mutations at this site abolished this function (Cosulich et al., Curr. Biol., 7:913-920 [1997]; and Yin et al., Nature, 369: 321-323 [1994]).

Furthermore, synthetic cell permeable peptides binding to this pocket in Bcl-2 induce apoptosis in vitro and have in vivo activity in suppressing human myeloid leukemia growth. (See, Holinger et al., J. Biol. Chem., 274:13298-13304 [1999]; Michael et al., Science, 275:983-986 [1997]; and Wang et al., Cancer Res., 60:1498-1502 [2000]).

Anti-sense oligonucleotides and single chain antibodies have been shown to enhance tumor cell chemosensitivity (See e.g., J. C. Reed, Adv. Pharm., 41:501-553 [1997]; Strasser et al., Biochem. Biophys. Acta, 1333:F151-F189 [1997]; Webb et al., Lancet, 349:1137-1141 [1997]; Ziegler et al., J. Natl. Cancer. Inst., 89:1027-1036 [1997]; Piche et al., Cancer Res., 58:2134-2140 [1998]; DiPaola et al., Semin. Oncol., 26:112-116 [1999]; and Cotter et al., J. Clin. Oncol. 18:1812-1823 [2000]).

For example, the anti-sense oligonucleotide (G3139) (Raynaud et al., J. Pharmacol. Exp. Ther., 281:420-427 [1997]) designed to hybridize to sequence in Bcl-2 mRNA, was shown to inhibit Bcl-2 expression, induce apoptosis and inhibit cell growth in human breast cancer cells having Bcl-2 overexpression. (See, Chen et al., Proceedings of American Society of Clinical Oncology, 2000). Combination treatments of G3139 and docetaxel provided synergistic effects and complete tumor regression in vivo.

Additonally, several groups have reported designing small molecule non-peptide inhibitors of Bcl-2/Bcl-$X_L$. The first small molecule inhibitor of Bcl-2 (Wang et. al., Proc. Natl. Acad. Sci. USA, 97:7124-7129 [2000]) was designed using a computerized structure-based database screening strategy. Wang et al. screened the Available Chemical Directory of more than 200,000 small organic compounds and found one class of small organic molecule (HA14-1) that binds to the BH3 binding site in Bcl-2 (See 1 in Chart 1). HA14-1 effectively induced apoptosis in human acute myeloid leukemia (HL-60) cells overexpressing Bcl-2

Chart 1. Small molecule inhibitors of Bcl-2 (or Bcl-$X_L$) reported by other investigators.

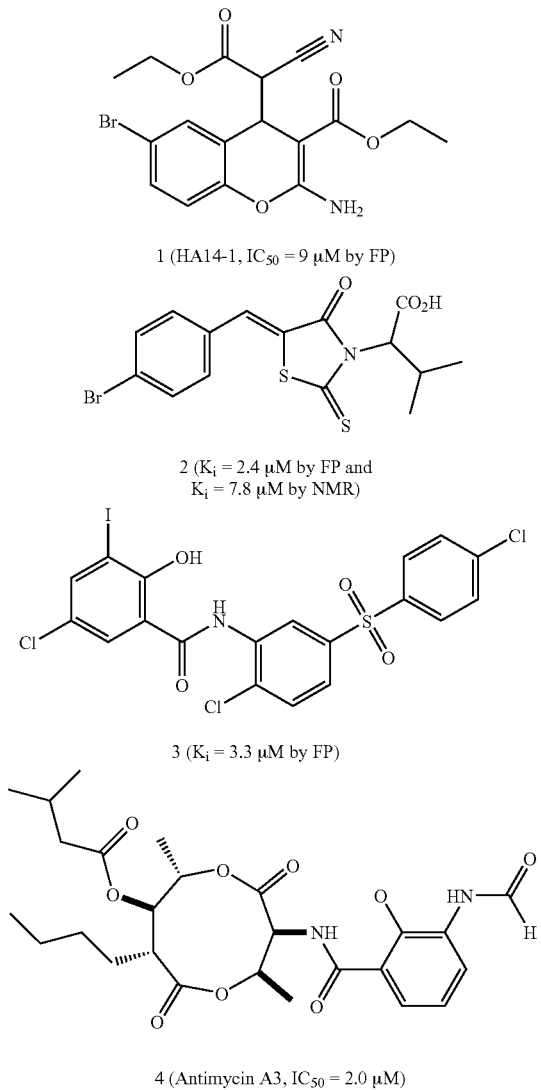

1 (HA14-1, $IC_{50}$ = 9 µM by FP)

2 ($K_i$ = 2.4 µM by FP and
$K_i$ = 7.8 µM by NMR)

3 ($K_i$ = 3.3 µM by FP)

4 (Antimycin A3, $IC_{50}$ = 2.0 µM)

protein. The potency of this small organic inhibitor is moderate, $IC_{50}$=9 µM in binding assay.

Subsequently three new classes of small molecule inhibitors of Bcl-2 or Bcl-$X_L$ were reported (Degterev et al., Nat. Cell. Biology., 3:173-182 [2001]; Tzung et al., Nat. Cell Biology, 3:183-191 [2001]) designed using high-throughput screening assays based upon fluorescene polarization. Degterev et al. screened a library of 16,320 chemicals and identified two different classes of small molecule inhibitors of Bcl-$X_L$. Representative compounds are shown in Chart 1 (Compounds 2 and 3). (Degterev et al., supra). Tzung et al. identified antimycin A (Compound 4 in Chart 1), a known antibiotic, as a small molecule inhibitor of Bcl-2/Bcl-$X_L$ with an $IC_{50}$ value of 2 µM. (Tzung et al., supra). These three studies showed that a small organic molecule inhibitors that bind to the BH3 domain in Bcl-2/Bcl-$X_L$ can inhibit the anti-apoptotic function of these proteins, which in turn induces apoptosis in cells with Bcl-2/Bcl-$X_L$ overexpression. These findings strongly indicated that it is possible to design novel small molecule inhibitors that block the interactions between Bcl-2/Bcl-$X_L$ and pro-apoptotic proteins (peptides), for example, Bak, Bad and Bax, and inhibit the biological function of Bcl-2/Bcl-$X_L$.

Inhibition of the anti-apoptotic functions of Bcl-2 and/or Bcl-$X_L$ using nonpeptide small molecules provides a promising strategy for overcoming the resistance of some cancers to chemotherapy and radiation therapy. In particular, Bcl-$X_L$ represents a highly attractive molecular target for the design of novel anticancer drugs for treatment of ER negative breast cancers. Accordingly, in preferred embodiments the present invention provides, non-peptide, drug-like, cell permeable small molecules that bind to this pocket of Bcl-2 and/or Bcl-$X_L$ and block the anti-apoptotic functions of these proteins in cancer cells with Bcl-2 protein overexpression.

DETAILED DESCRIPTION OF THE INVENTION

The present invention relates to small molecule antagonists of Bcl-2 family proteins such as Bcl-2 and/or Bcl-$X_L$. In particular, the present invention provides non-peptide cell permeable small molecules (e.g., tricyclo-dibenzo-diazocine-dioxides) that bind to a pocket in Bcl-2/Bcl-$X_L$ that block the anti-apoptotic function of these proteins in cancer cells and tumor tissues exhibiting Bcl-2 protein overexpression. In preferred embodiments, the small molecules of the present invention are active at the BH3 binding pocket of Bcl-2 family proteins (e.g., Bcl-2, Bcl-$X_L$, and Mcl-1). The compositions and methods of the present invention are useful therapeutics for cancerous diseases either alone or in combination with chemotherapeutic or other drugs. Exemplary compositions and methods of the present invention are described in more detail in the following sections: I. Binding activity of Bcl-2 and Bcl-$X_L$; II. Preferred compositions; III. Biological testing; IV. Therapeutic agents combined with the present compositions; and V. Pharmaceutical considerations.

I. Binding Activity of Bcl-2 and Bcl-$X_L$

Although an understanding of the mechanism is not necessary to practice the present invention and the present invention is not so limited, it is contemplated that the anti-apoptotic affects of Bcl-2 and Bcl-$X_L$ proteins are attributed, at least in part, to their ability to heterodimerize with pro-apoptotic Bcl-2 family members such as Bak, Bax and Bad. The experimental structures of Bcl-2 and Bcl-$X_L$ showed that BH1 (Bcl-2 homology domain 1), BH2 and BH3 domains of Bcl-2 and Bcl-$X_L$ form a hydrophobic binding pocket (the BH3 binding pocket) into which Bak or Bad BH3 domain binds. (See e.g., S. W. Muchmore et al., Nature, 381:335-341 [1996]; M. Aritomi et al., J. Biol. Chem., 272:27886-27892 [1997]; S. Michael et al., Science, 275:983-986 [1997]; and A. M. Petros et al., Protein Sci., 9:2528-2534 [2000]; and A. M. Petros et al., Proc. Natl. Acad. Sci. USA, 98:3012-3017 [2001]). This binding pocket in Bcl-2/Bcl-$X_L$ is essential for anti-apoptotic function. (See e.g., X. M. Yin et al., Nature, 369:321-323 [1994]; S. C. Cosulich et al., Curr. Biol., 7:913-920 [1997]; S. Michael et al., supra; and A. M. Petros et al., supra). Thus, preferred embodiments of the present invention provide small molecules that bind to the BH3 binding site in Bcl-2 and/or Bcl-$X_L$ that are capable of blocking the hetero-dimerization of Bcl-2 and/or Bcl-$X_L$ with the pro-apoptotic members of the Bcl-2 protein family (e.g., Bad, Bak, and Bax etc.) such that the anti-apoptotic function of Bcl-2 and/or Bcl-$X_L$ is antagonized and apoptosis is induced in cells with Bcl-2 and/or Bcl-$X_L$ overexpression. In some of these embodiments, the present invention further provides one or more additional anticancer agents (e.g., taxol, taxotere, and docetaxel) administered in combination with the disclosed small molecules inhibitors of Bcl-2 and/or Bcl-$X_L$.

The present invention provides small molecule inhibitors of Bcl-2 and Bcl-$X_L$ that have several advantages over currently available Bcl-2 family antagonists (e.g., antisense oligonucleotides, antibodies, and peptides) such as better oral availability, better stability, and lower cost.

II. Preferred Compositions

The chemical synthesis of the compositions of the present invention is well within the ability of those of ordinary skill in the art, particularly known compounds, for example, Compound 6. The chemical modifications of these compounds are readily preformed using standard synthetic methods available to those skilled in the art. Table 1, shown below, provides specific exemplary compounds derived from the composition Formulas of the present invention.

TABLE 1

| Formula No./Structure* | Example: Compound No./Structure |
|---|---|
| I | 5 |
| II | 6 |
| III | 7 |
| IV | 8 |

TABLE 1-continued

| Formula No./Structure* | Example: Compound No./Structure |
|---|---|
| V | 9 |
| VI | 10 |
| VII | 11 |

In addition to the specific compounds described in Table 1, the summary of the invention provides additional functional groups and deritives readily synthesized from the compositions set forth in Formulas I-VII.

III. Biological Testing

In some embodiments, the following in vitro binding and cellular assays were used to determine the activity and specificity of candidate Formulas, and deritive compounds thereof, as small molecule inhibitors of cl-2 and/or Bcl-$X_L$ suitable for use in the methods of the present invention.

In particular, in one embodiment candidate small molecule inhibitors were identified, for example, by using a modeled 3D structure of Bcl-2 to screen components from the National Cancer Institute's 3D-database of 225,000 small molecules using the publicly available DOCK program. (S. Makino and I. D. Kuntz, J. Comput. Chem. 18:1812-1825 [1997]).

A. Bcl-2 Binding Assay

In preferred embodiments, a sensitive and quantitative in vitro binding assay was conducted using an established fluorescence polarization (FP) based method. (See, Wang et a1, Cancer Res. 2000, 60, 1498-1502). Using the method, a binding affinity of 0.3 µM ($IC_{50}$) was obtained for the Bak-BH3 peptide to the Bcl-2, which is consistent with the value reported in literature. (Wang et al., Proc. Natl. Acad. Sci. USA, 97:7124-7129 [2000]). Using the binding assay, candidate small molecules were screened for their binding activity. The binding affinity of the 35 candidate small molecules was tested initially at a dose of 100 µM in this binding assay. Of which, 7 compounds showed inhibitory activity more than 50% at the initial 100 μM dose level and were classified as active. The other 28 compounds had less than 50% of inhibition at the 100 μM dose level and were classified as inactive. Further dose dependent binding experiments were carried out on the 7 active compounds to determine their $IC_{50}$ values. All 7 active compounds displayed a dose dependent inhibition of the Bak peptide binding to Bcl-2. The chemical structures and $IC_{50}$ values of these 7 active compounds, respectively refered to in FIG. 4 and throughout the specification as compounds 5-11, are provided in FIG. 4.

Figure 4:
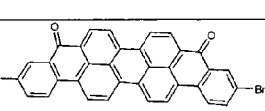
FIG. 4 shows the chemical structure and binding affinity of active compounds in certain embodiments of the present invention.
Figure 4:
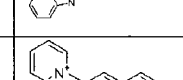
Figure 4:
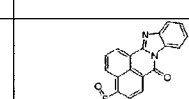
Figure 4:
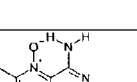
Figure 4:
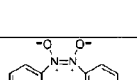
Figure 4:
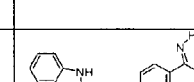
Figure 4:
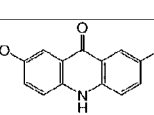

As shown in FIG. 4, all 7 active compounds have an $IC_{50}$ value better than 20 μM. Compound 7 is the most potent compound in the binding assay, with an $IC_{50}$ value of 1.6 μM. The other 6 compounds have an $IC_{50}$ value from 5.8 to 14.0 μM. FIG. 4 also shows that all 7 active compounds belong to different chemical classes and their structures are different from previously reported Bcl-2 inhibitors. (See, compounds 1-4 in Chart 1).

In previous approaches used in the art it was necessary to laboriously screen very large numbers of candidate compounds to find potential Bcl-2/Bcl-$X_L$ inhibitors. For example, in one study it was necessary to screen 16,320 compounds in a high throughput screening approach to find two chemical classes of small molecule inhibitors of Bcl-2/Bcl-$X_L$. (See, Degterev et al., Nat. Cell. Biology, 3:173-182 [2001]). In contrast, in the present invention, testing only 35 compounds selected from a structure-based 3D-database resulted in the finding of 7 distinct classes of small molecule inhibitors of Bcl-2. The present invention indicates that the structure-based computer screening strategies described herein are effective for tools for discovering novel small molecule inhibitors of Bcl-2 and/or Bcl-$X_L$.

The present invention demonstrates that active compounds, for example, Compound 6, inhibit the binding of the Bak-BH3 peptide to Bcl-2 in vitro. (FIG. 1). Because of the importance of this surface pocket to the anti-apoptotic function of Bcl-2, it appears that the binding of Compound 6 to Bcl-2 inhibits the anti-apoptotic function of Bcl-2 in cells. This inhibition in turn induces apoptosis in cells overexpressing Bcl-2 protein, as shown herein.

Figure 2:
FIG. 2 illustrates the level of Bcl-2 protein expression in cancer cell lines as detected by Western blotting. 401 g cell lysates are resolved in 16% SDS polyacryamide gel electrophoresis, detected by the monoclonal anti-BCL2 antibody (Oncogene Research Products, Cambridge, Mass.), and visualized by an ECL Western blotting detection system (Amersham Pharmacia Biotech UK Limited, Buckinghamshire, England).

Bcl-2 protein expression in human breast and other cancer cell line is characterized herein. Cell lines MCF-7, MDA-231 and MDA-361 express high levels of Bcl-2; MDA-468, BT474 and MDA-435 express median levels. T47D expresses a very low but detectable, whereas MDA-453 does not express detectable Bcl-2. (FIG. 2). Human myeloid leukemia cell HL-60 expresses the highest level of Bcl-2 protein among all the cell lines examined. Accordingly, MDA-231 and HL-60 cell lines with high Bcl-2 expression are positive cells and MDA-453 and T47D are negative control cells. In some embodiments, the level of Bcl-2 protein expression is detected by Western blotting.

In one embodiment, using a Hoechst Dye assay, cells are treated with different doses of candidate compounds for 12 hours and the apoptotic cells are visually identified and counted under the microscope. Induction of apoptosis was evident after the treatment with Compound 6 at 10 μM in MDA-453 and T47D cell lines, cells with low Bcl-2 expression. At these doses, significant apoptosis in MDA-231 and HL-60 cells was induced.

Figure 3:
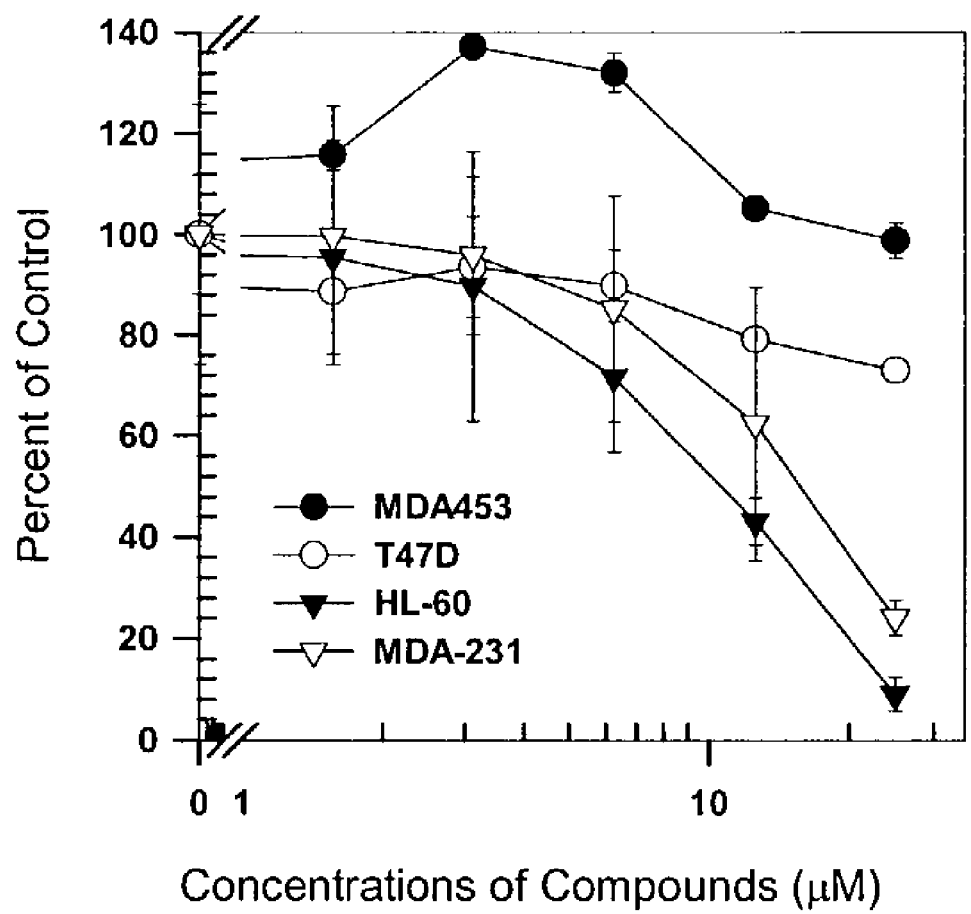
FIG. 3 illustrated the effects of Compound 6 on cell viability. Cells are plated in 24-well plates, incubated with the compound at appropriate concentrations for 14 hr. Cell viability is determined by trypan blue exclusion with hemocytometer. Percent of viable cells, as compared with untreated cells, is plotted against drug concentration.

In still other embodiments, the Annexin-V FACS assay provides a more quantitative assessment of the ability of cabdidate compounds (e.g., Compound 6) to induce of apoptosis in HL-60 and MDA-231 cells. For example, MDA-231 cells treated with 0 (untreated), 4 and 10 μM of Compound 6 for 24 hours provide 0, 13% and 20.0% apoptotic cells, respectively, while HL-60 cells treated with 0, 5, 10, and 20 μM of Compound 6 for 24 hours provided 0, 24%, 31% and 67% of apoptotic cells, respectively. (FIG. 3). Therefore, Compound 6 induces apoptosis in a highly dose-dependent manner in MDA-231 and HL-60 cell lines with Bcl-2 protein overexpression.

B. Inhibition of Cell Viability

Binding experiments showed that the 7 active compounds of the present invention compete with the Bak BH3 peptide binding to Bcl-2 in vitro. The inhibitory activity of the 7 active compounds on cell viability and proliferation was observed in two different assays. First, in some embodiments, the trypan blue exclusion method was used to determine the effect of an inhibitor on cell viability in which cells were treated with the inhibitor for 24 hours. Second, in some other embodiments, the MTT assay was used to determine the activity of an inhibitor on cell proliferation where cells were treated for four days. All the 7 active compounds were tested using the HL-60 cell line that expresses the highest level of Bcl-2 protein among all the cancer cell lines examined.

All the seven compounds except for compound 10 had an $IC_{50}$ value better than 50 μM. Compound 6 is the most potent compound in the cellular assay, with an $IC_{50}$ value of 10 μM, as shown in FIG. 3. In further testing using the MTT assay where cells were treated for 4 days, compound 6 showed potent inhibition of cell growth with an $IC_{50}$ value of 4 μM. Because of its potent cellular activity, compound 6 was used in subsequent biological experiments.

The ability of Compound 6 to inhibit cell viability in cancer cells with Bcl-2 protein overexpression has been demonstrated. When HL-60 or MDA-231 cells are exposed to Compound 6, the compound provides dose-dependent cell killing in the trypan-blue exclusion cell survival assay with $IC_{50}$ values of 12 μM and 15 μM, respectively. The ability of Compound 6 to inhibit cell viability is highly specific and correlates well with the Bcl-2 protein expression level in these cancer cells.

IV. Therapeutic Agents Combined with the Present Compositions

Wide ranges of therapeutic agents find use with the compositions and methods of the present invention. In the broadest sense, any therapeutic agent that can be co-administered with the compounds described herein, or associated with these compounds is suitable for us in the present invention.

Some embodiments of the present invention provide methods of administering a subject an effective amount of a small molecule inhibitor of Bcl-2 and/or Bcl-$X_L$ (and enantiomers, derivatives, and pharmaceutically acceptable salts thereof) and at least one anticancer agent (e.g., a conventional anticancer agent, such as, chemotherapeutic drugs, and/or radiation therapy). In some of these embodiments, the subject has a disease characterized by intercellular overexpression of Bcl-2 family proteins (e.g., Bcl-2 and/or Bcl-$X_L$).

Anticancer agent mechanisms suitable for use with the present invention include, but are not limited to, agents that induce apoptosis, agents that induce nucleic acid damage, agents that inhibit nucleic acid synthesis, agents that affect microtubule formation, and agents that affect protein synthesis or stability.

Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-α, etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

In some embodiments, the present invention provides administration of an effective amount of small molecule Bcl-2/Bcl-$X_L$ modulator (e.g., inhibitor) and a taxane (e.g., Docetaxel) to a subject having a disease characterized by the overexpression of Bcl-2 family protein(s) (e.g., Bcl-2 and/or Bcl-$X_L$). The taxanes (e.g., Docetaxel) are an effective class of anticancer chemotherapeutic agents. (See e.g., K. D. Miller and G. W. Sledge, Jr. Cancer Investigation, 17:121-136 [1999]). While the present invention is not limited to any particular mechanism, taxane-mediated cell death likely proceeds through intercellular microtubule stabilization and subsequent induction of the apoptotic pathway. (See e.g., S. Haldar et al., Cancer Research, 57:229-233 [1997]). In many systems, Bcl-$X_L$ functions as a negative control on this pathway.

In some other embodiments, cisplatin and taxol are administered with the small molecule Bcl-2/Bcl-$X_L$ modulators (e.g., inhibitors). Cisplatin and Taxol have a well-defined action of inducing apoptosis in tumor cells (See e.g., Lanni et al., Proc. Natl. Acad. Sci., 94:9679 [1997]; Tortora et al., Cancer Research 57:5107 [1997]; and Zaffaroni et al., Brit. J. Cancer 77:1378 [1998]). Taxol therapeutics are active against a wide-range of tumor types including, but not limited to, breast cancer and colon cancer (Akutsu et al., Eur. J. Cancer 31A:2341 [1995]).

However, treatment with these and other chemotherapeutic agents is difficult to accomplish without incurring significant toxicity. The agents currently in use are generally poorly water soluble, quite toxic, and given at doses that affect normal cells as wells as diseased cells. For example, Paclitaxel has shown excellent antitumor activity in a wide variety of tumor models such as the B 16 melanoma, L1210 leukemias, MX-1 mammary tumors, and CS-1 colon tumor xenografts. However, the poor aqueous solubility of paclitaxel presents a problem for human administration. Accordingly, currently used paclitaxel formulations require a cremaphor to solubilize the drug. The human clinical dose range is 200-500 mg. This dose is dissolved in a 1:1 solution of ethanol:cremaphor and diluted to one liter of fluid given intravenously. The cremaphor currently used is polyethoxylated castor oil given by infusion. Direct administration (e.g., subcutaneous) of Paclitaxel results in local toxicity and low levels of activity.

Any pharmaceutical routinely used in cancer therapy finds use in the present invention. Conventional anticancer agents that are suitable for administration with the disclosed small molecule Bcl-2/Bcl-$X_L$ modulators (e.g., inhibitors) include, but are mot limited to, adriamycin, 5-fluorouracil, etoposide, camptothecin, actinomycin-D, mitomycin C, and cisplatin. Agents may be prepared and used in combined therapeutic compositions, as kits, or in combination with an immunotherapeutic.

In some embodiments of the present invention, the therapeutic small molecule Bcl-2/Bcl-$X_L$ modulators (e.g., inhibitors) treatments further comprise one or more agents that directly cross-link nucleic acids (e.g., DNA) to facilitate DNA damage leading to a synergistic, antineoplastic agents of the present invention. Agents such as cisplatin, and other DNA alkylating agents may be used. Cisplatin has been widely used to treat cancer, with efficacious doses used in clinical applications of 20 mg/M$^2$ for 5 days every three weeks for a total of three courses. The compositions of the present invention are deliverable via any suitable method, including, but not limited to, injection intravenously, subcutaneously, intratumorally, intraperitoneally, or topically (e.g., to mucosal surfaces).

Agents that damage DNA also include compounds that interfere with DNA replication, mitosis, and chromosomal segregation. Such chemotherapeutic compounds include, but are not limited to, adriamycin, also known as doxorubicin, etoposide, verapamil, podophyllotoxin, and the like. These compounds are widely used in clinical settings for the treatment of neoplasms, and are administered through bolus injections intravenously at doses ranging from 25-75 Mg/M$^2$ at 21 day intervals for adriamycin, to 35-50 Mg/M$^2$ for etoposide intravenously or double the intravenous dose orally.

Agents that disrupt the synthesis and fidelity of nucleic acid precursors and subunits also lead to DNA damage and find use as chemotherapeutic agents in the present invention. In this regard, a number of nucleic acid precursors have been developed. Particularly useful are agents that have undergone extensive testing and are readily available. As such, agents such as 5-fluorouracil (5-FU) are preferentially used by neoplastic tissue, making this agent particularly useful for targeting to neoplastic cells. The doses delivered may range from 3 to 15 mg/kg/day, although other doses may vary considerably according to various factors including stage of disease, amenability of the cells to the therapy, amount of resistance to the agents and the like.

In preferred embodiments, the anticancer agents used in the present invention are those that are amenable co-administration with the disclosed small molecule Bcl-2/Bcl-$X_L$ modulators (e.g., inhibitors) or are otherwise associated with the disclosed compounds such that they can be delivered into a subject, tissue, or cell without loss of fidelity of anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate and other similar anti-cancer agents, those of skill in the art are referred to any number of instructive manuals including the Physician's Desk reference and to Goodman and Gilman's "Pharmaceutical Basis of Therapeutics" ninth edition, Eds. Hardman et al., 1996.

In some embodiments, the anticancer drugs are attached to the small molecule Bcl-2/Bcl-$X_L$ modulators (e.g., inhibitors) with photocleavable linkers. For example, several heterobifunctional, photocleavable linkers that find use with the present invention are described by Ottl et al. (Ottl et al., Bioconjugate Chem., 9:143 [1998]). These linkers can be either water or organic soluble. They contain an activated ester that can react with amines or alcohols and an epoxide that can react with a thiol group. In between the two groups is a 3,4-dimethoxy6-nitrophenyl photoisomerization group, which, when exposed to near-ultraviolet light (365 nm), releases the amine or alcohol in intact form. Thus, the therapeutic agent, when linked to the compositions of the present invention using such linkers, are preferably released in biologically active or activatable form through exposure of the target area to near-ultraviolet light.

In an exemplary embodiment, the alcohol group of taxol is reacted with the activated ester of an organic-soluble linker. This product in turn is reacted with the partially-thiolated surface of an appropriate dendrimers (the primary amines of the dendrimers can be partially converted to thiol-containing groups by reaction with a sub-stoichiometric amount of 2-iminothiolano). In the case of cisplatin, the amino groups of the drug are reacted with the water-soluble form of the linker. If the amino groups are not reactive enough, a primary amino-containing active analog of cisplatin, such as Pt(II) sulfadiazine dichloride (See, Pasani et al., Inorg. Chim. Acta 80:99 [1983] and Abel et al., Eur. J. Cancer 9:4 [1973]) can be used. Thus conjugated, the drug is inactive and will not harm normal cells. When the conjugate is localized within tumor cells, it is exposed to laser light of the appropriate near-UV wavelength, causing the active drug to be released into the cell.

Similarly, in other embodiments of the present invention, the amino groups of cisplatin (or an analog thereof) is linked with a very hydrophobic photocleavable protecting group, such as the 2-nitrobenzyloxycarbonyl group (Pillai, V. N. R. Synthesis: 1-26 [1980]). When exposed to near-UV light (about 365 nm), the hydrophobic group is cleaved, leaving the intact drug. Since the drug itself is hydrophilic, it diffuses out of the dendrimer and into the tumor cell, where it initiates apoptosis.

An alternative to photocleavable linkers are enzyme cleavable linkers. A number of photocleavable linkers have been demonstrated as effective anti-tumor conjugates and can be prepared by attaching cancer therapeutics, such as doxorubicin, to water-soluble polymers with appropriate short peptide linkers (See e.g., Vasey et al., Clin. Cancer Res., 5:83 [1999]). The linkers are stable outside of the cell, but are cleaved by thiolproteases once within the cell. In a preferred embodiment, the conjugate PK1 is used. As an alternative to the photocleavable linker strategy, enzyme-degradable linkers, such as Gly-Phe-Leu-Gly (SEQ ID NO:1) may be used.

The present invention is not limited by the nature of the therapeutic techniques employed. For example, other conjugates that find use with the present invention include, but are not limited to, using conjugated boron dusters for BNCT (Capala et al., Bioconjugate Chem., 7:7 [1996]), the use of radioisotopes, and conjugation of toxins such as ricin.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins, antisense nucleic acids, membrane disruptive agents and the like, used alone or in combination. Indeed, any type of antibiotic may be used including, but not limited to, anti-bacterial agents, anti-viral agents, anti-fungal agents, and the like.

In still further embodiments, the compounds of the present invention are associated with targeting agents capable of specifically targeting a particular cell type (e.g., tumor cell). Generally, the compound associated with a targeting agent, targets neoplastic cells through interaction of the targeting agent with a cell surface moiety and is taken into the cell through receptor mediated endocytosis.

Any moiety known to be located on the surface of target cells (e.g., tumor cells) finds use with the present invention. For example, an antibody directed against such a moiety targets the compositions of the present invention to cell surfaces containing the moiety. Alternatively, the targeting moiety may be a ligand directed to a receptor present on the cell surface or vice versa. Similarly, vitamins also may be used to target the therapeutics of the present invention to a particular cell.

In some embodiments of the present invention, the targeting moiety also functions to identify a particular tumor characterized by expression of a receptor that the targeting agent (ligand) binds with, for example, tumor specific antigens include, but are not limited to, carcinoembryonic antigen, prostate specific antigen, tyrosinase, ras, a sialyly lewis antigen, erb, MAGE-1, MAGE-3, BAGE, MN, gp100, gp75, p97, proteinase 3, a mucin, CD81, CID9, CD63; CD53, CD38, CO-029, CA125, GD2, GM2 and O-acetyl GD3, M-TAA, M-fetal or M-urinary find use with the present invention. Alternatively, the targeting moiety may be a tumor suppressor, a cytokine, a chemokine, a tumor specific receptor ligand, a receptor, an inducer of apoptosis, or a differentiating agent.

Tumor suppressor proteins contemplated for targeting include, but are not limited to, p16, p21, p27, p53, p73, Rb, Wilms tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, R2, CD81, CO029, TI-1, L6 and SAS. Of course these are merely exemplary tumor suppressors.

In further preferred embodiments, targeting is directed to factors expressed by an oncogene (e.g., bcl-2 and/or bcl-$X_L$). These factors include tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

Receptors and their related ligands that find use in the context of the present invention include, but are not limited to, the folate receptor, adrenergic receptor, growth hormone receptor, luteinizing hormone receptor, estrogen receptor, epidermal growth factor receptor, fibroblast growth factor receptor, and the like.

Hormones and their receptors that find use in the targeting aspect of the present invention include, but are not limited to, growth hormone, prolactin, placental lactogen, luteinizing hormone, foilicle-stimulating hormone, chorionic gonadotropin, thyroid-stimulating hormone, leptin, adrenocorticotropin (ACTH), angiotensin I, angiotensin II, α-endorphin, amelanocyte stimulating hormone (α-MSH), cholecystokinin, endothelin I, galanin, gastric inhibitory peptide (GIP), glucagon, insulin, amylin, lipotropins, GLP-1 (7-37) neurophysins, and somatostatin.

In addition, the present invention contemplates that vitamins (both fat soluble and non-fat soluble vitamins) used as targeting agents may be used to target cells that have receptors for, or otherwise take up these vitamins. Particularly preferred for this aspect are the fat soluble vitamins, such as vitamin D and its analogues, vitamin E, Vitamin A, and the like or water soluble vitamins such as Vitamin C, and the like.

In some embodiments of the present invention, any number of cancer cell targeting groups are associated with the present compounds. Thus, the compounds associated with targeting groups are specific for targeting cancer cells (i.e., much more likely to attach to cancer cells and not to healthy cells).

In preferred embodiments of the present invention, targeting groups are associated (e.g., covalently or noncovalently bound) to gossypol compounds with either short (e.g., direct coupling), medium (e.g., using small-molecule bifunctional linkers such as SPDP, sold by Pierce Chemical Company), or long (e.g., PEG bifunctional linkers, sold by Shearwater Polymers) linkages.

In some embodiments, the small molecule Bcl-2/Bcl-$X_L$ modulators (e.g., inhibitors) are associated with dendrimers (e.g., PAMAM), liposomes, or other carriers. Those skilled in the art will be able to readily design therapeutic molecules that take advantage of the multivalent structure of dendrimers.

In preferred embodiments of the present invention, the targeting agent is an antibody or antigen binding fragment of an antibody (e.g., Fab units). For example, a well-studied antigen found on the surface of many cancers (including breast HER2 tumors) is glycoprotein p185, which is exclusively expressed in malignant cells (Press et al., Oncogene 5:953 [1990]). Recombinant humanized anti-HER2 monoclonal antibodies (rhuMabHER2) have even been shown to inhibit the growth of HER2 overexpressing breast cancer cells, and are being evaluated (in conjunction with conventional chemotherapeutics) in phase III clinical trials for the treatment of advanced breast cancer (Pegrarn et al., Proc. Am. Soc. Clin. Oncol., 14:106 [1995]). Park et al. have attached Fab fragments of rhuMabHER2 to small unilamellar liposomes, which then can be loaded with the chemotherapeutic doxorubicin (dox) and targeted to HER2 overexpressing tumor xenografts (Park et al., Cancer Lett., 118:153 [1997] and Kirpotin et al., Biochem., 36:66 [1997]). These dox-loaded "immunoliposomes" showed increased cytotoxicity against tumors compared to corresponding non-targeted dox-loaded liposomes or free dox, and decreased systemic toxicity compared to free dox.

In some embodiments, antibodies allow targeting of antigens or immunogens (e.g., tumor, tissue or pathogen specific antigens) on various biological targets (e.g., pathogens, tumor cells, normal tissue). Such antibodies include, but are not limited to, polyclonal, monoclonal, chimeric, single chain, Fab fragments, and an Fab expression libraries.

In some preferred embodiments, the antibodies recognize tumor specific epitopes (e.g. TAG-72 (Kjeldsen et al., Cancer Res. 48:2214-2220 [1988]; U.S. Pat. No. 5,892,020; 5,892,019; and 5,512,443); human carcinoma antigen (U.S. Pat. No. 5,693,763; 5,545,530; and 5,808,005); TP1 and TP3 antigens from osteocarcinoma cells (U.S. Pat. No. 5,855, 866); Thomsen-Friedenreich (TF) antigen from adenocarcinoma cells (U.S. Pat. No. 5,110,911); "KC-4 antigen" from human prostrate adenocarcinoma (U.S. Pat. No. 4,708,930 and 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. No. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA)(U.S. Pat. No. 4,914,021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., Carbohydr. Res. 178:271-292 [1988]), MSA breast carcinoma glycoprotein termed (Tjandra et al., Br. J. Surg. 75:811-817 [1988]); MFGM breast carcinoma antigen (Ishida et al., Tumor Biol. 10: 12-22 [1989]); DU-PAN-2 pancreatic carcinoma antigen (Lan et al., Cancer Res. 45:305-310 [1985]); CA125 ovarian carcinoma antigen (Hanisch et al., Carbohydr. Res. 178:29-47 [1988]); YH206 lung carcinoma antigen (Hinoda et al., Cancer J., 42:653-658 [1988]). Each of the foregoing references is specifically incorporated herein by reference.

Various procedures known in the art are used for the production of polyclonal antibodies. Various host animals can be immunized for the production of antibodies by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants are used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that produces antibody molecules using continuous cell lines in culture may be used. (See e.g., Harlow and Lane, *Antibodies: A Laboratory Manual*, Cold Spring Harbor Laboratory Press, Cold Spring Harbor, N.Y.). These include, but are not limited to, the hybridoma technique originally developed by Köhler and Milstein (Köhler and Milstein, Nature, 256: 495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A.80:2026-2030 [1983]) or by transforming human B cells with EBV virus in vitro (Cole et al., in *Monoclonal Antibodies and Cancer Therapy*, Alan R. Liss, pp. 77-96 [1985]).

According to the invention, techniques described for the production of single chain antibodies (U.S. Pat. No. 4,946, 778; herein incorporated by reference) can be adapted to produce specific single chain antibodies. An additional embodiment of the invention utilizes the techniques described for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule are generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

For breast cancer, the cell surface may be targeted with folic acid, EGF, FGF, and antibodies (or antibody fragments) to the tumor-associated antigens MUC1, cMet receptor and CD56 (NCAM).

A very flexible method to identify and select appropriate peptide targeting groups is the phage display technique (See e.g., Cortese et al., Curr. Opin. Biotechol., 6:73 [1995]), which can be conveniently carried out using commercially available kits. The phage display procedure produces a large and diverse combinatorial library of peptides attached to the surface of phage, which are screened against immobilized surface receptors for tight binding. After the tight-binding, viral constructs are isolated and sequenced to identify the peptide sequences. The cycle is repeated using the best peptides as starting points for the next peptide library. Eventually, suitably high-affinity peptides are identified and then screened for biocompatibility and target specificity. In this way, it is possible to produce peptides that can be conjugated to dendrimers, producing multivalent conjugates with high specificity and affinity for the target cell receptors (e.g., tumor cell receptors) or other desired targets.

Related to the targeting approaches described above is the "pretargeting" approach (See e.g., Goodwin and Meares, Cancer (suppl.) 80:2675 [1997]). An example of this strategy involves initial treatment of the patient with conjugates of tumor-specific monoclonal antibodies and streptavidin. Remaining soluble conjugate is removed from the bloodstream with an appropriate biotinylated clearing agent. When the tumor-localized conjugate is all that remains, a small molecule Bcl-2/Bcl-$X_L$ modulators (e.g., inhibitors)-linked, biotinylated agent is introduced, which in turn localizes at the tumor sites by the strong and specific biotin-streptavidin interaction.

In some embodiments of the present invention, the targeting agents (moities) are preferably nucleic acids (e.g., RNA or DNA). In some embodiments, the nucleic acid targeting moities are designed to hybridize by base pairing to a particular nucleic acid (e.g., chromosomal DNA, mRNA, or ribosomal RNA). In other embodiments, the nucleic acids bind a ligand or biological target. Nucleic acids that bind the following proteins have been identified: reverse transcriptase, Rev and Tat proteins of HIV (Tuerk et al., Gene, 137(1):33-9 [1993]); human nerve growth factor (Binkley et al., Nuc. Acids Res., 23(16):3198-205 [1995]); and vascular endothelial growth factor (Jellinek et al., Biochem., 83(34):10450-6[1994]). Nucleic acids that bind ligands are preferably identified by the SELEX procedure (See e.g., U.S. Pat. No. 5,475,096; 5,270,163; and 5,475, 096; and in PCT publications WO 97/38134, WO 98/33941, and WO 99/07724, all of which are herein incorporated by reference), although many methods are known in the art.

V. Pharmaceutical Considerations

To illustrate the delivery of therapeutic agents, the following discussion focuses mainly on the delivery of small molecule modulators (e.g., inhibitors) of Bcl-2 and/or Bcl-$X_L$ (and enantiomers, derivatives, and pharmaceutically acceptable salts thereof) for the treatment of cancer, however, the present invention is not intended to be limited to compositions and methods specifically described herein.

The present invention provides pharmaceutical compositions comprising at least one small molecule modulator (e.g., inhibitor) of Bcl-2 and/or Bcl-$X_L$ (and enantiomers, derivatives, and pharmaceutically acceptable salts thereof), and in preferred embodiments, at least one conventional anticancer agent.

Preferably, the compositions of the present invention are administered in any sterile, biocompatible pharmaceutical carrier, including, but not limited to, saline, buffered saline, dextrose, and water. In preferred embodiments of the present invention, pharmaceutically acceptable carriers are biologically inert; in other embodiments, they are not. In some embodiments, the pharmaceutical compositions of the present invention may contain one agent (e.g a small molecule modulator (e.g., inhibitor) of Bcl-2 and/or Bcl-$X_L$ and enantiomers, derivatives, and pharmaceutically acceptable salts thereof). In other embodiments, the pharmaceutical compositions may contain a mixture of at least two agents (e.g., two or more small molecule modulators of Bcl-2 and/or Bcl-$X_L$, and/or one small molecule modulator of Bcl-2 and/or Bcl-$X_L$ and another anticancer agent). In still further embodiments, the pharmaceutical compositions of the present invention are administered to a subject under one or more of the following conditions: at different periodicities, durations, concentrations, and administration routes, etc.

The compositions and methods of the present invention find use in treating diseases or altering physiological states characterized by overexpression of Bcl-2 family proteins (e.g., Bcl-2, Bcl-$X_L$, Mcl-1, A1/BFL-1, and BOO-DIVA, etc.). The invention provides methods for inducing apoptosis by administering antagonists of anti-apoptotic Bcl-2 family proteins, including, but not limited to, Bcl-2, Bcl-$X_L$, Mcl-1, A1/BFL-1, and BOO-DIVA.

The present invention contemplates administering small molecule modulators (e.g., inhibitors) of Bcl-2 and/or Bcl-$X_L$ (and enantiomers, derivatives, and pharmaceutically acceptable salts thereof) in accordance with acceptable pharmaceutical delivery methods and preparation techniques. For example, the compounds and suitable anticancer agents can be administered to a subject intravenously in a pharmaceutically acceptable carrier such as physiological saline. Standard methods for intracellular delivery of pharmaceutical agents are used (e.g., delivery via liposome). Those skilled in the art are familiar with intravenous drug delivery methods. In some embodiments, the formulations of the present invention are useful for parenteral administration, such as intravenous, subcutaneous, intramuscular, and intraperitoneal. Therapeutic co-administration of some contemplated anticancer agents (e.g., therapeutic polypeptides) can also be accomplished using gene therapy techniques. Dispersions can also be prepared in glycerol, liquid polyethylene glycols, triacetin, and mixtures thereof and in oils. Under ordinary conditions of storage and use, these preparations contain a preservative to prevent the growth of microorganisms.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

As is well known in the medical arts, the dosage for a particular patient depends upon many factors, including the patient's size, body surface area, age, gender, general health, the compound being administered, the time and route of administration, and possible interactions with other drugs being administered.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated. In preferred embodiments, the gossypol compounds are administered orally to a patient orally.

Pharmaceutical compositions suitable for use in the present invention include compositions wherein the active ingredients are contained in an effective amount to achieve the intended purpose. For example, an effective amount of small molecule modulators (e.g., inhibitors) of Bcl-2 and/or Bcl-$X_L$ (and enantiomers, derivatives, and pharmaceutically acceptable salts thereof) may be that amount that induces apoptosis in a cell or tissue having elevated levels of a Bcl-2 family protein as compared to normal nonpathological examples of the particular cells or tissues. Determination of effective amounts is well within the capability of those skilled in the art especially in light of the disclosure provided herein.

In addition to the active ingredients, preferred pharmaceutical compositions may contain suitable pharmaceutically acceptable carriers comprising excipients and auxiliaries that facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate. Of course, any material used in preparing any unit dosage form should be pharmaceutically acceptable and substantially non-toxic in the amounts employed. In addition, the active compound may be incorporated into sustained-release preparations and devices.

Ingestible formulations of the present compositions may further include any material approved by the United States Department of Agriculture for inclusion in foodstuffs and substances that are generally recognized as safe (GRAS), such as, food additives, flavorings, colorings, vitamins, minerals, and phytonutrients. The term phytonutrients as used herein, refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Compositions comprising a compound of the invention formulated in a pharmaceutical acceptable carrier may be prepared, placed in an appropriate container, and labeled for treatment of an indicated condition. For gossypol compounds, conditions indicated on the label may include treatment of conditions related to faulty regulation of apoptosis, hyperproliferative diseases, cancers, acquired immune deficiency syndrome (AIDS), degenerative conditions, and vascular diseases. The pharmaceutical compositions may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose is estimated initially from cell culture assays. Then, preferably, the dosage is formulated in animal models (particularly murine models) to achieve a desirable circulating concentration range that induces apoptosis in cells with elevated levels of Bcl-2 family proteins. A therapeutically effective dose refers to that amount of small molecule modulators (e.g., inhibitors) of Bcl-2 and/or Bcl-$X_L$ (and enantiomers, derivatives, and pharmaceutically acceptable salts thereof) that ameliorate symptoms of the disease state (e.g., unregulated cell proliferation diseases, including, but not limited to, cancer). Toxicity and therapeutic efficacy of such compounds is determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from cell culture assays and additional animal studies can be used in formulating a range of dosage, for example, mammalian use (e.g., humans, Equus caballus, Felis catus, and Canis familiaris, etc.). The dosage of such compounds lies preferably, however the present invention is not limited to this range, within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation. Other pharmaceutical compositions may be administered daily or several times a day.

In some embodiments, normal dosage amounts may vary from 0.1 to 100,000 micrograms, up to a total dose of about 1 g, depending upon the route of administration. Guidance as to particular dosages and methods of delivery is provided in the literature. (See, U.S. Pat. No. 4,657,760; 5,206,344; or 5,225,212, all of which are herein incorporated by reference). Administration of some agents to a patient's bone marrow may necessitate delivery in a manner different from intravenous injections.

In some embodiments, small molecule modulators (e.g., inhibitors) of Bcl-2 and/or Bcl-$X_L$ (and enantiomers, derivatives, and pharmaceutically acceptable salts thereof) are administered to a patient at a dosage range of about 10 to 100 mg/day, from about 20 to 50 mg/day, and most preferably from about 30 to 40 mg/day. In particularly preferred embodiments, the compounds are administered to a patient (e.g., orally) in a tolerable daily dose (e.g., 30 to 40 mg/day) shown to have some biologic activity.

In preferred embodiments, the primary endpoint of dosing studies is obtained when the maximum tolerated dose of compound (at a particular daily dose, e.g., 30 mg/day) optionally administered in combination with a particular conventional anticancer agent is established. In some embodiments, dose-limiting toxicity (DLT) is established when a given sample (e.g., a cell, tissue, or fluid sample) shows >500 neutrophils or any other toxicity which is Grade 3 or 4 at any time while the patient is being studied.

In still some other embodiments, to evaluate dose escalation a minimum of 9 weeks of treatment is required for 2 patients started at each dose level. The maximum tolerated dose (MTD) is defined as the dose at which 33% of patients experience DLT. If the MTD is not reached by a particular dose then this dose level is defined as the MTD. In preferred embodiments, doses are allocated to patients according to the criteria described in the Continual Reassessment Method. (J. O'Quigley et al., Biometrics 46:33-48 [1990]; called Time-to-Event CRM or (TITE-CRM). Briefly, the TITE-CRM method assumes a model for the time to occurrence of toxic response as a function of dose, and allows information from all patients enrolled in the trial to be employed when allocating a new patient to a dose level. Because this method is very flexible in terms of the number of patients treated at each dose, subjects may be continuously recruited throughout a trial, without recruitment pauses, as long as patients are treated at a dose consistent with the safety profile.

In preferred embodiments, the subject has a disease characterized by the overexpression of a Bcl-2 family protein (e.g., Bcl-2, Bcl-$X_L$, Mcl-1, A1/BFL-1, and BOO- DIVA, etc.). In some of embodiments, diseases characterized by overexpression of a Bcl-2 family protein include, but are not limited to, hyperproliferative diseases, cancers, acquired immune deficiency syndrome (AIDS), degenerative conditions, and vascular diseases. In still further embodiments, the cancers suitable for treatment by the present compositions and methods, include, but are not limited to, breast cancer, prostate cancer, lymphoma, skin cancer, pancreatic cancer, colon cancer, melanoma, ovarian cancer, brain cancer, liver cancer, bladder cancer, non-small lung cancer, cervical carcinoma, myeloma, adrenal carcinoma, leukemia, neuroblastoma, and glioblastoma. However, the present invention is not intended to be limited to treating any particular type of cancer.

In some embodiments, diseases suspected of being characterized by having elevated levels of Bcl-2 family protein(s) suitable for treatment by the present invention are selected by obtaining a sample of interest (e.g., cells, tissues, fluids, etc.) suspected of having high levels of Bcl-2 family proteins (e.g., Bcl-2, Bcl-$X_L$, Mcl-1, A1/BFL-1, and BOO-DIVA, etc.), measuring the levels of Bcl-2 family proteins in the sample using one or more well established immunohistochemical techniques (e.g., ELISA and Western blots, etc.), and comparing the levels of Bcl-2 family proteins in the sample with levels of Bcl-2 family proteins in relevant reference nonpathological samples. In other embodiments, diseases suspected of being characterized by having elevated levels of one or more Bcl-2 family proteins (e.g., Bcl-2, Bcl-$X_L$, Mcl-1, A1/BFL-1, and BOO-DIVA, etc.) are selected by comparing levels of one or more markers (e.g., polynucleotides, polypeptides, lipids, etc.) in a sample (e.g., cells, tissues, fluids, etc.) that directly or indirectly indicate elevated levels of Bcl-2 family proteins in the sample as compared to levels of these markers relevant nonpathological samples. In still further embodiments, diseases suspected of being characterized by having elevated levels of Bcl-2 family proteins (e.g., Bcl-2, Bcl-$X_L$, Mcl-1, A1/BFL-1, and BOO-DIVA, etc.) are selected from diseases that do not respond or that stop responding to treatment with one or more conventional anticancer therapies (e.g., chemotherapy, radiation therapy, and/or surgical intervention).

In some embodiments, standard immunohistochemical techniques are employed on samples obtained from patients following, or during, treatments with the methods and compositions of the present invention to determine changes in the levels of Bcl-2 family proteins (e.g., Bcl-2, Bcl-$X_L$, and Bax, etc.). For example, in some embodiments, immunohistochemical techniques using antibodies to Bcl-2 (DAKO, Carpinteria, Calif.), Bcl-$X_L$, and/or Bax (Zymed, South San Francisco, Calif.) are used to determine the levels of these Bcl-2 proteins in patient samples. In preferred embodiments results from the immunohistochemical studies are interpreted using well-established criteria known to those in the art, any cytoplasmic or nuclear staining will be considered positive. The expression levels of Bcl-2, Bcl-$X_L$, and Bax will be determined by counting at least 1,000 neoplastic cells in each case and expressed as a percentage. Expression will be considered high when the percentage of positive cells is >25% for Bcl-2, and Bcl-$X_L$, and >50% for Bax. (See e.g., G. Rassidakis et al., Amer. J. Path., 159:527-535 (2001); and S. Shi et al., J. Histochem. Cytochem., 39:741-748 [1991]). In other embodiments, intermittent samples of whole blood will be obtained for fluorescence activated cell sorting (FACS) analysis for Bcl-2 and Bcl-$X_L$ expression in peripheral blood lymphocytes (PBLs) and for immunomagnetic selection of circulating epithelial cells.

In preferred embodiments, following treatment diseased cells and tissues are subjected to assays for cell viability, induction of apoptosis, such as, morphological changes, DNA integrity, mitochondria pathways, alterations of expression of Bcl-2 family proteins, and caspase activation as well as upstream and downstream effectors of caspases and caspase inhibitors. Those skilled in the art will be able to readily design and execute assays to test these and an number of other cellular and biochemical parameters in the treated cells and tissues.

In cases where exemplary compounds of Formula II, for example Compound 6, are sufficiently basic or acidic to form stable nontoxic acid or base salts, administration of the compounds as salts is appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, alpha-glycerophosphate, benzensulfonate, camphorsulfonate, fumarate, lactate, maleate, mandelate, mucate, pamoate, succinate and the like.

Suitable inorganic salts may also be formed, including hydrochloride, sulfate, nitrate, phosphate, bicarbonate, and carbonate salts.

Pharmaceutically acceptable salts may be obtained using standard procedures well known in the art, for example, by reacting a sufficiently basic compound, for example, an amine with a suitable acid affording a physiologically acceptable anion. Alkali metal (for example, sodium, potassium or lithium) or alkaline earth metal (for example, calcium) salts of carboxylic acids can also be made.

The compounds of Formula II, for example Compound 6, can be formulated as pharmaceutical compositions and administered to a mammalian host, for example, a human patient in a variety of forms adapted to the chosen route of administration, i.e., orally or parenterally, by intravenous, intramuscular, topical or subcutaneous routes.

Sterile injectable solutions are prepared by incorporating the active compound in the required amount in the appropriate solvent with various of the other ingredients enumerated above. as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pureform, i.e., when they are liquids. However, it will generally be desirable to administer them to the skin as compositions or formulations, in combination with a dermatologically acceptable carrier, which may be a solid or a liquid.

Useful solid carriers include finely divided solids, for example, talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants, for example, fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners, for example, synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula II (for example, compound 6) to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508) (each incorporated herein by reference in its entirety).

EXAMPLES

The following examples are provided to demonstrate and further illustrate certain preferred embodiments of the present invention and are not to be construed as limiting the scope thereof.

Example 1

Homology Modeling

The sequence of human Bcl-2 was obtained from Gene Bank (entry gi4557355). The NMR structure of Bcl-$X_L$ (pdb code: 1BXL from the protein databank[40]), which has 45% amino acid sequence identity, 56% sequence similarity and 3% gaps with Bcl-2, was used as the template (Michael et al., Science, 275:983-986 [1997]). The structure of Bcl-2 was built using the homology-modeling program MODELLER (version 4.0). (See, MODELLER web site http://guitar.rockefeller.edu/modeller/modeller.html). MODELLER is most frequently used for comparative modeling of protein three-dimensional structure. More generally, MODELLER models protein 3D structure by satisfaction of spatial restraints (Sali et al., PROTEINS: Structure, Function, and Genetics, 23:318-326 [1995]; Sali, A. Curr. Opin. Biotech., 6:437-451 [1995]). The restraints used in the comparative modeling of Bcl-2 structure were automatically derived from the experimental 3D structure of Bcl-$X_L$ by the MODELLER program. The output of MODELLER is the 3D structure models of Bcl-2 that satisfy these restraints as well as possible. The optimization is carried out by the variable target function procedure employing methods of conjugate gradients and molecular dynamics with simulated annealing. (See, MODELLER web site http://guitar.rockefeller.edu/modeller/modeller.html).

Further refinement was done using the molecular dynamics program CHARMM (version 27b2) (Brooks et al., J. Comput. Chem., 4:187-217 [1983]). Hydrogen atoms were assigned to the modeled structure using the program QUANTA (QUANTA, Molecular Simulations Inc., San Diego, Calif.). The Bak BH3 peptide was placed into the Bcl-2 BH3 domain binding site in the same orientation as in the NMR structure of Bcl-$X_L$ in complex with the Bak BH3 peptide (1BXL in protein databank) (Michael et al., Science, 275:983-986 [1997]). The complex structure was solvated by inserting it into a 60 Å diameter TIP3P water sphere and deleting solvent molecules that have heavy atoms at less then 2.5 Å from any protein heavy atom. The MD simulation was done using the all atom parameter set from the CHARMm force field as implemented in QUANTA, a constant dielectric, $\epsilon=1$ and constant temperature, T=300 K. The leap frog method with 1 fs time step was applied for numerical integration. Long-range electrostatic forces were treated with the force switch method with a switching range of 8-12 Å. Van der Waals forces were calculated with the shift method and a cutoff of 12 Å. The nonbond list was kept to 14 Å and updated heuristically. Solvent waters were kept from evaporating by using a spherical miscellaneous mean field potential as implemented in CHARMM (Brooks et al., J. Comput. Chem., 4:187-217 [1983]). The solvated protein was energy minimized using 100 cycles using the Steepest Descent method and additional 1000 cycles using the Adopted-Basis Newton Raphson method. This was followed by 3.0 ns MD simulation. The simulation was performed on an Origin2000 computer at the Advanced Biomedical Computing Center at the National Institutes of Health.

Example 2

Structure-Based 3D-Database Searching

The refined structure of Bcl-2 from the Bak/Bcl-2 complex, obtained after the 3 ns MD simulation, was used for structure-based database searching of the NCI-3D database (Milne et al., J. Chem. Inf. Comput. Sci., 34:1219-1224 [1994]). Program DOCK (version 4.0.1) was employed (Ewing and Kuntz, J. Comput. Chem., 18:1175-1189 [1997]). All residues within 8 Å from the Bak peptide were included in the binding-site used for screening. United atom KOLLMAN charges were assigned for the protein using the BIOPOLYMER menu in the Sybyl program (Sybyl, Tripos, Inc., St. Louis, Mo.). Because of its general applicability, the Geisterger method as implemented in Sybyl was used to assign charges to the compounds. National Cancer Institute's 3D database of 206,876 small molecules and natural products that can be accessed by the public (Milne et al., J. Chem Inf. Comput. Sci., 34:1219-1224 [1994]) was searched.

The interactions between the Bak BH3 peptide and Bcl-2 in the modeled complex structures define the crucial binding elements between them. Thus, the spheres used in the DOCK program were defined in part by the coordinates of the Bak BH3 peptide in the modeled complex structure with Bcl-2. The conformational flexibility of the compounds from the database was considered and their position and conformation were optimized using single anchor search and torsion minimization. Fifty configurations per ligand building cycle and 100 maximum anchor orientations were used in the anchor-first docking algorithm. All docked configurations were energy minimized using 10 iterations and 2 minimization cycles. This combination of parameters resulted in an average of 26 CPU seconds per compound on a Silicon Graphics Indigo2 Impact with a 195 MHz R10,000 CPU. Several filters were used during database screening: compounds with more than 10 flexible bonds, or with less than 10 heavy atoms, or with more than 50 heavy atoms were not considered. These essentially excluded highly flexible, very small or very large molecules. A scaling factor of 0.5 was used for the electrostatic interaction calculations. The sum of the electrostatic and Van der Waals interactions as calculated in the DOCK program was used as the ranking score. The top scoring 500 compounds were analyzed for structural diversity. All organometallic compounds were discarded. Chemical samples of 80 compounds were selected and 35 samples were used in biological testing.

Example 3

Chemical Samples of the "Open" Compounds

All 35 chemical samples were dissolved at 10 mM in dimethyl sulfoxide (DMSO) prior to biological experiments.

A. Chemistry:

All chemical reagents were commercially available. Melting points were determined on a MelTemp II apparatus and are uncorrected. Silica gel chromatography was performed on silica gel 60, 230-400 mesh (E. Merck). $^1$H spectra were recorded on a Varian Mercury instrument at 300 MHz or on a Bruker AC-250 instrument at 250, and $^{13}$C NMR Spectra were recorded on a Bruker AC-250 instrument at 62.9 MHz. Spectra were referenced to the solvent in which they were run (7.24 ppm for $^1$H CDCl$_3$). Elemental analyses were performed by Atlantic Microlab, Inc., Atlanta, Ga. FAB mass spectra were performed on a VG-7070-EHF Mass Spectrometer, at unit resolution (isotopic mass), in the positive and/or negative ion mode. Sample matrix: 3-nitrobenzyl alcohol (NBA).

B. Analytical Analysis of the Compounds:

Compound 5. FABMS 613.2 (M+H)$^+$. Insoluble in either DMSO or chloroform.

Compound 6. The data for this compound are provided in the synthesis section below.

Compound 7. $^1$H NMR(DMSO-d$_6$, 300 MHz), 8.57 (d, 1H, J=3.3 Hz), 8.55 (d, 1H, J=3.3 Hz), 8.39-8.43 (m, 2H), 7.69 (t, 1H, J=3.3 Hz), 7.67 (t, 1H, J=3.3 Hz), 7.42-7.50 (m, 3H). FABMS 305.4(M)$^-$.

Compound 8. $^1$H NMR(CDCl$_3$, 300 MHz) 9.56 (d, 1H, J=2.7 Hz), 8.57 (m, 1H), 8.22 (m, 1H), 7.91 (m, 1H), 7.71 (m, 2H), 7.52(m, 1H), 7.32(m, 1H). FABMS 222.1 (M)$^+$.

Compound 9. FABMS 1241.8 (M)$^+$ or 352.3 (M)$^-$.

Compound 10. FABMS 538 (M)$^-$.

Compound 11. $^1$H NMR(DMSO-d$_6$, 300 MHz) 10.92 (s, 1H), 9.48 (bs, 1H), 9.38 (s, 1H), 9.18 (bs, 1H), 8.0-8.2 (m, 4H), 7.90 (d, 1H, J=7.2 Hz), 7.83 (d, 1H, J=8.4 Hz), 7.35 (dd, 1H, J=2.4; 7.2 Hz), 7.22 (t, 1H, J=8.4 Hz), 7.05 (t, 1H, J=7.2 Hz), 6.80 (d, 1H, J=2.4 Hz), 6.61(dd, 1H, J=2.4; 8.4 Hz). FABMS 330.1(M+H)$^+$.

C. Synthesis:

5,5'-Dimethoxy-2,2'-dinitrobibenzyl (Compound 41)

To a solution of potassium tertbutoxide (16.11 g, 136.40 mmol) in ether (126.8 ml) and DMSO (6.34 ml) at −10° C. was added slowly 5-methyl-2-nitrotoluene (20 g, 119.65 mmol). The reaction mixture was stirred at −10° C. for 45 min then allowed to warm to room temperature and stirred for an additional 3 h. The reaction was quenched by adding water (50 ml) dropwise and the mixture was extracted with CH$_2$Cl$_2$ (3×150 ml). The organic layers were gathered, dried with MgSO$_4$, filtered, and concentrated. The crude product was recrystallized in CHCl$_3$ to afford compound 41 (12.83 g, 38.57 mmol, 64%) as brownish crystals. mp 193-195° C. $^1$H NMR (DMSO-d$_6$) δ, 8.08 (d, 2H, J=9.03 Hz), 7.07 (dd, 2H, J=2.69; 9.03 Hz), 6.96 (d, 2H, J=2.69 Hz), 3.88 (s, 4H), 3.40 (s, 6H). $^{13}$C NMR (DMSO-d$_6$, 62.9 MHz) δ, 162.65, 141.62, 138.52, 127.46, 116.80, 112.79, 55.97, 33.47. Anal. Calcd for C$_{16}$H$_{16}$N$_2$O$_6$: C, 57.83; H, 4.85; N, 8.43. Found C, 57,70; H, 4.90; N, 8.37.

5,5'-Dimethoxy-2,2'-diaminobibenzyl (Compound 42)

A solution of 5,5'-dimethoxy-2,2'-dinitrobibenzyl (compound 41) (12.0 g, 36.11 mmol) in ethanol (271 ml) was treated with 10% Pd/C (1.2 g) and hydrazine hydrate (7.37 ml, 236.52 mmol) was added dropwise over 10 min. The reaction mixture was stirred at r.t. for 30 min. then refluxed for 2 h. The hot solution was filtered through a short pad of celite and the catalyst was washed with hot benzene (500 ml) and hot 95% ethanol (250 ml). The filtrates were concentrated under reduced vacuum to give the crude product, which was recrystallized in benzene to afford compound 42 (9.64 g, 35.39 mmol, 98%) as dark green needles: mp 69-71° C. $^1$H NMR (DMSO-d$_6$ 250 MHz) δ ppm: 6.87-6.55 (m, 6H), 4.47 (broad s, 4H), 3.66 (s, 6H), 2.65 (s, 4H). $^{13}$C NMR (DMSO-d$_6$, 62.9 MHz) δ ppm: 150.95, 139.62, 126.87, 115.58, 114.96, 111.73, 55.19, 30.13. Anal. Calcd for C$_{16}$H$_{20}$N$_2$O$_2$: C, 70.56; H, 7.40; N, 10.29. Found C, 70.19; H, 7.45; N, 10.21.

2,9-Dimethoxy-11,12-dihydrodibenzo [c,g] [1,2] diazocine-5,6-dioxide (Compound 6a) (and 5,5'-dimethoxy-2,2'-dinitrosobibenzyl (Compound 6b).

A solution of compound 42 (2.46 g, 9.04 mmol) and sodium tunsgtate dihydrate (0.42 g, 1.26 mmol) in 95% ethanol (27.13 ml) and water (9.04 ml) was cooled to 5° C. and treated dropwise with 30% H$_2$O$_2$ (4.61 ml). The reaction mixture was stirred for 5 h at 5° C., then 10 ml of a saturated aqueous solution of NH$_4$Cl was added, and extracted with CH$_2$Cl$_2$ (3×30 ml). The organic phase was dried over Na$_2$SO$_4$, filtered, and concentrated under reduced pressure to afford the crude product. Recrystallization in CH$_2$Cl$_2$/hexanes afforded 1.22 g (4.06 mmol, 45%) of green crystals. The mother solution was concentrated under reduced pressure, and the residue purified by flash chromatography on silica gel with hexanes/ethyl acetate: 3/1 as eluant to give an additional 0.431 g (1.47 mmol, 16%) of compounds 6a and 6b as green crystals. mp: 136-138° C.

Compound 6a (closed isomer). $^1$H NMR (DMSO-d$_6$, 250 MHz) δ, 7.42 (d, 2H, J=8.55 Hz), 6.89-6.83 (m, 4H), 3.76 (s, 6H), 3.07 (distorted d, 4H). $^1$H NMR (CDCl$_3$, 250 MHz) δ, 7.37 (d, 2H, J=8.79 Hz), 6.80 (dd, 2H, J=2.69; 8.79 Hz), 6.66 (d, 2H, J=2.69 Hz), 3.84 (s, 6H), 3.38 and 3.01 (A$_2$B$_2$, 4H).

Compound 6b (open isomer). $^1$H NMR (DMSO-d$_6$, 250 MHz) δ, 7.19 (d, 2H, J=2.69 Hz), 6.84-6.79 (m, 4H), 6.34 (d, 2H, J=9.03 Hz), 4.36 (s, 4H), 3.91 (s, 6H). $^1$H NMR (CDCl$_3$, 250 MHz) δ, 6.97 (d, 2H, J=2.44 Hz), 6.73 (dd, 2H, J=2.44; 9.03 Hz), 6.54 (d, 2H, J=9.03 Hz), 4.42 (s, 4H), 3.94 (s, 6H). Anal. Calcd for C$_{16}$H$_{16}$N$_2$O$_4$: C, 63.99; H, 5.37, N, 9.33. Found C, 63.72; H, 5.48, N, 9.28. FABMS 300.9 (M+H)$^+$.

Example 4

Bcl-2 FP Binding Assay

The fluorescence-labeled 16-mer peptide tracer Flu-Bak-BH3 (sequence GQVGRQLAIIGDDINR derived from Bak BH3 domain) was synthesized and labeled at the amino terminus. The 46-kDa recombinant soluble GST-fused Bcl-2 protein was purchased from Santa Cruz Biotechnology (Santa Cruz, Calif.). The reaction was carried out in a total volume of 20 µl per well containing 10 µl of 1× phosphate-buffered saline, 5 µl of the GST-Bcl-2 protein, and 5 µl of peptide tracer. The reaction was incubated at room temperature for 20 min. The reading was taken at λex=485 nm and λem=535 nm using the Ultra Reader (Tecan U.S. Inc, Research Triangle Park, N.C.). A series of validation experiments were performed by analyzing the maximal and minimal signals obtained by the background, buffer, Bcl-2 protein, tracer and mixture of Bcl-2 protein and tracer. The K$_d$ of binding between Bcl-2 protein and the 16-mer fluorescence-labeled peptide was determined by titration of Bcl-2 protein at a concentration range of 5.4 nM to 540 nM and fluorescent tracer concentration range of 0.145 nM to 1,450 nM. The optimal binding was obtained at a final concentration of 290 nM fluorescent tracer and 270 nM Bcl-2 protein.

To verify the specificity, binding of the labeled peptide was competed with nonlabeled 16-mer peptide. The data indicate that nonlabeled 16-mer peptide was able to abrogate binding of the labeled tracer, with an $IC_{50}$ of approximately 0.3 µM, a value similar to the value reported in the literature.

Initial screening of all compounds was carried out at 100 µM. Five microliters of the test compound were added in reaction buffer to each of the wells containing tracer and Bcl-2 protein at the same concentration determined before. The final concentration of DMSO in all compounds was less than 1%. The final reading was taken after a 10-min incubation at room temperature. For $IC_{50}$ determination of active compounds, 6 to 7 point serial dilutions were made in triplicate starting at 100 µM.

Cells and Reagents. Human breast cell lines (T47D, MDA-231, MDA-453), and human Leukemia cells HL-60 were obtained from the American Type Culture Collection (ATCC). All tumor cell lines were grown and maintained in RPMI 1640 medium containing 10% FBS, except MDA-MB-231, which used Dulbecco's modified Eagle's medium as basal medium. Cultures were maintained in a humidified incubator at 37° C. and 5% $CO_2$.

Example 5

Cell Viability and Growth Assays

Cell viability was determined by the trypan blue assay. Trypan blue is a polar dye that cannot cross intact cell membranes but crosses the membranes of necrotic cells and apoptotic cells undergoing secondary necrosis. Thus, it is a useful, rapid and simple screening assay for viable cells. In this assay, cells (5,000 cells/well) were plated in triplicate in 24-well plates with culture medium and various amounts of FBS. Various concentrations of drugs were added to the cells. Trypan blue dye was added 24 hours later and the percentage of viable cells were determined.

A. Cell Growth Assay:

Cell growth was determined by the MTT assay. The MTT assay is a colorimetric assay that measures the reduction of 3-(4,5-dimethylthiazol-2-yl)-2,5,-diphenyl tetrazolium bromide (MTT) by mitochondrial succinate dehydrogenase. The MTT enters the cells and passes into the mitochondria where it is reduced to an insoluble, colored, formazen product. The cells are then solubilised with an organic solvent (isopropanol) and the released, solubilised formazen reagent is measured spectrophotometrically. Since reduction of MTT can only occur in metabolically active cells the level of activity is a measure of the viability of the cells. Cells (2,000-4,000 cells/well) were grown in medium with FBS and various concentrations of drugs were added to the cells at the beginning. Four days later, MTT was added to each well and incubated for four hours at 37° C. Absorbency was measured with the Dynatech Model MR700.

B. Assay of Apoptosis:

For flow cytometry apoptosis assay, cell pellets were resuspended in 1× binding buffer (10 mM HEPES pH 7.4, 0.15 M NaCl, 5 mM KCl, 1 mM $MgCl_2$, 1.8 mM $CaCl_2$) containing 1:100 dilution of Annexin V-FITC (Trevigen) and 50 µg/ml of propidium iodide and incubated at 4° C. for 15 min. The fluorescence of Annexin V-FITC and propidium iodide of individual cells were analyzed by FACscan.

Example 6

NMR Experiments

A. Expression and Purification of the Bcl-$X_L$ Protein:

The recombinant Bcl-$X_L$ proteins was overexpressed from *Escherichia coli* BL21(DE3) and pET15b (Novagen, Darmstadt, Germany) expression vector with an N-terminal His tag. In this construct the putative C-terminal membrane-anchoring region (residues 214-237) and a loop between helix 1 and helix 2 (residues 49-88) were removed to facilitate the purification of the protein. This loops is previously shown to be dispensable for the anti-apoptotic activity of the protein (Muchmore et al., Nature, 381:335-341 [1996]). The cells were grown in the minimum medium using $^{15}NH_4Cl$ as the sole nitrogen source to produce uniformly $^{15}N$ labeled protein (Cai et al., J. Biomol. NMR, 11:97-102 [1998]; and Jansson et al., J. Biomol. NMR, 7:131-141 [1996]). The protein was purified with Ni-NTA resin (Novagen) and His-tag was cleaved by Thrombin digestion. The protein was further purified with NI-NTA resin and Benzamidine Sepharose resin (Pharmacia, Piscataway N.J.).

B. NMR Data Acquisition and Analysis:

The NMR experiments were performed on Varian Inova 500 (Varian Medical Systems, Inc., Palo Alto, Colo.) with pulse field gradient (PFG) HSQC with water flip back to maximize the signal intensity and to minimize thedestruction from the water signal. (Grzesiek and Bax, J. Am. Chem. Soc., 115:12593-12594 [1993]; Sheppard et al., Abstracts of Papers of the American Chemical Society, 213: 81 [1993]) (300 µM Bcl-$X_L$, 50 mM Phosphate buffer pH 7.3, 2 mM DTT at 25° C.). HSQC spectra of Bcl-$X_L$ was recorded prior to (free Bcl-$X_L$) and after the addition of the concentrated compound 6 solution (the final concentration of compound 6 in the sample was 300 µM). Then two spectra were compared to identify the chemical shifts induced by the additions of the inhibitor. The NMR data were processed with programs, pipp and nmrDraw. (Delaglio et al., J. Biomol. NMR, 6:277-293 [1995]; and Garrett et al., J. Magn. Reson. Ser., (B)95:214-220 [1991]).

Scheme 1. Synthetic scheme of compound 6.

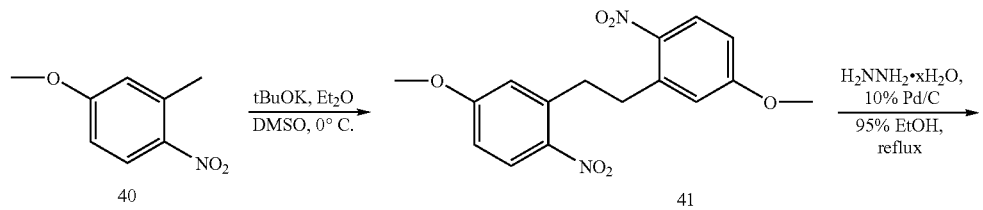

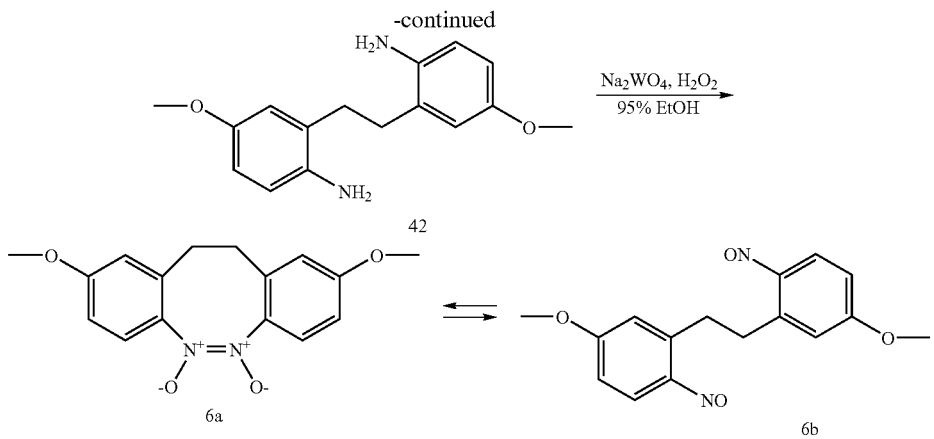

Example 7

Chemical Synthesis of Formula II (e.g., Compound 6)

The general synthesis procedure of Formula II (e.g., compound 6) is illustrated in Scheme I, according to a method developed by Bown and Greene (D. H. Bown, Synthesis and investigation of aryl azo dioxide-bisnitroso systems, Ph.D. Thesis [Thesis supervisor, Professor Frederick D. Greene TI, Department of Chemistry, Mass. Inst. Tech, 1983]). Briefly, commercially available 3-methyl-4-nitroanisole (compound 40) was dimerized to give compound 41 in 64% yield by oxidation with tBuOK and ether in DMSO. The diamino derivative of compound 42 was obtained in excellent yield by reducing compound 41 in the presence of hydrazine hydrate and a catalytic amount of palladium. Oxidation of compound 42 with hydrogen peroxide and sodium tungstate dihydrate in ethanol gave compound 6 in 61% yield. It was previously shown that Formula II (for example, compound 6) was in tautomeric equilibrium (1:3:68 at 295.70 K in chloroform). Based upon NMR data, it is estimated that the ratio between compounds 6a and 6b is 1:3.69-3.79 in chloroform or 1:2.52 in DMSO in room temperature, respectively.

Example 8

Chemical Structure Verification of the Active Compounds

The structures of these small molecule inhibitors of Bcl-2 are shown in FIG. 4. Mass spectral analysis on the samples of the active 7 compounds were performed. The results are shown in FIG. 5. All five compounds gave mass in agreement with the calculated mass based upon the chemical structures. However, two compounds, 9 and 10 were found to have an observed mass not in agreement with the calculated mass, suggesting that the chemical structures for these two compounds as recorded in the NCI database are incorrect.

Subsequently $^1$H NMR spectra for the five active compounds were performed. The $^1$H NMR spectrum for compound 5 is not determined, because it is insoluble in either DMSO or chloroform. The $^1$H NMR spectra for compounds 6, 7, 8 and 11 are consistent with their chemical structures.

Compound 6 potently inhibits the cell viability (FIG. 3) and growth, thus representing a novel class of cell permeable small molecule inhibitor of Bcl-2 and a promising lead compound for further design and chemical modifications. Accordingly, the compound 6 was synthesized in order to confirm conclusively its chemical structure.

Example 9

Specificity of Compound 6 in Inhibition of Cell Viability

It is shown that Bcl-2 inhibitor compound 6 blocks the binding of the Bak BH3 peptide to Bcl-2 in vitro and potently inhibits cell viability and growth in HL-60 cell line with high Bcl-2 expression. The specificity of Bcl-2 inhibitors, for example, compound 6 were further tested in cancer cell lines with different levels of Bcl-2 expression to investigate whether compound 6 can achieve specific inhibition of cell viability and whether its cellular activity is dependent upon the level of Bcl-2 protein in cancer cells.

For this purpose, Bcl-2 protein expression was first characterized in human breast and other cancer cell lines and the results are shown in FIG. 2. Of the cell lines examined, human myeloid leukemia cell HL-60 expresses the highest level of Bcl-2 protein among all the cell lines examined. MDA-231 (subelone 2LMP derived from during the present invention) expresses a high level of Bcl-2; T47D expresses a very low but detectable, whereas MDA-453 does not express detectable Bcl-2. Accordingly, MDA-231 and HL-60 cell lines with high Bcl-2 expression as the positive cells and MDA-453 and T47D as the negative control cells to test the specificity of compound 6 in inhibition of cell viability using the trypan blue exclusion assay were selected, as well as in the apoptosis experiments. The results are shown in FIG. 3.

In HL-60 and MDA-231 cells, two cell lines with high Bcl-2 expression, compound 6 displays a dose-dependent inhibition of cell viability with an IC$_{50}$ value of 10 μM and 15 μM, respectively. In T47D cells, which have low but some level of Bcl-2 expression, compound 6 has a minimal activity at 25 μM. Furthermore, in MDA-453 cells, which have no detectable level of Bcl-2, compound 6 has no effect on cell viability at 25 μM. Therefore, the ability of compound 6 in inhibition of cell viability correlates with the Bcl-2 protein expression level in these cancer cells.

Example 10

Induction of Apoptosis

One central hypothesis was that the binding pocket formed by the BH1, BH2 and BH3 domains in Bcl-2 is essential for its anti-apoptotic function, and binding of a small molecule inhibitor, for example, compound 6 to this pocket may block the anti-apoptotic function of Bcl-2 and induce apoptosis in cells with Bcl-2 protein overexpression. To test the hypothesis, the ability and very importantly the specificity of compound 6, in inducing apoptosis in cancer cells with high or low level of Bcl-2 expression were evaluated.

The Annexin-V flow cytometry assay was used to obtain a quantitative assessment on the ability of compound 6 in induction of apoptosis in HL-60 and MDA-231 cells. MDA-231 cells treated with 0 (untreated), 5 and 10 µM of compound 6 for 24 hours exhibited 0, 13% and 20.0% apoptotic cells, respectively, while HL-60 cells treated with 0, 5, 10 and 20 µM of compound 6 for 24 hours had 0, 24%, 31% and 67% of apoptotic cells, respectively. Therefore, compound 6 induced apoptosis in a dose-dependent manner in MDA-231 and HL-60 cell lines with Bcl-2 protein overexpression.

Taken together, the results showed that compound 6 specifically induces apoptosis in a dose-dependent manner in cancer cells with high Blc-2 expression while has little effect on cancer cells with low or little Bcl-2 expression. The data suggest that overexpression of Bcl-2 is necessary to maintain the transformed state in these cancer cells and that blocking the Bcl-2 anti-apoptotic function with a small molecule inhibitor, for example, compound 6, induces apoptosis in cancer cells.

Example 11

Confirmation of the Binding of Compound 6 to Bcl-$X_L$ by NMR

Using the FP-based assay, it was shown that compound 6 binds to Bcl-2. However, the in vitro FP-based method simply shows that addition of a small molecule inhibitor reduces the intensity of FP. The most straightforward interpretation is that the small molecule inhibitor binds to Bcl-2 and displaces the binding of the fluorescence labeled Bak BH3 peptide. However, it is also possible that addition of the small molecule inhibitor simply causes the unfolding of the protein and thus reduces the binding of the fluorescence labeled Bak BH3 peptide to the protein. To rule out the latter possibility, NMR methods were employed to conclusively show that the change in FP signal upon addition of compound 6 is indeed due to the binding of compound 6 to the protein and not due to the unfolding of the protein.

Wild-type Bcl-2 behaves poorly in solution even if the putative hydrophobic transmembrane region is deleted and is thus not amenable to structure determination by either NMR spectroscopy or X-ray crystallography. Very recently, the problem of poor solubility of wild-type Bcl-2 was elegantly circumvented by using Bcl-2/Bcl-$X_L$ chimeras in which part of the putative unstructured loop of Bcl-2 was replaced with a shortened loop from Bcl-$X_L$. (Petros et al., Proc. Natl. Acad. Sci. USA, 98:3012-3017 [2001]). However, wild-type Bcl-$X_L$ is soluble if the putative hydrophobic transmembrane region is deleted. (Muchmore et al., Nature, 381:335-341 [1996]; and Michael et al., Science, 275:983-986 [1997]). Bcl-2 and Bcl-$X_L$ are closely related homologous proteins and have very similar 3D structures. It is recently determined the binding affinity of compound 6 to Bcl-$X_L$ using the FP binding assay and showed that compound 6 binds to Bcl-$X_L$ with an $IC_{50}$ value of 7 µM, similar to that binding to Bcl-2. Furthermore, Bcl-$X_L$ and Bcl-2 are structurally very similar. Thus, it is highly likely compound 6 binds to Bcl-2 and Bcl-$X_L$ in very similar binding modes. Since Bcl-$X_L$ behaves much better in solution (Muchmore et al., supra; Michael et al., supra), Bcl-$X_L$ was used in these NMR experiments.

The hetero-nuclear single quantum correlation (HSQC) spectrum of $^{15}N$ labeled Bcl-$X_L$ was measured with and without compound 6. The HSQC spectrum is also called a finger print spectrum because of its sensitivity to structural changes. The binding of compound 6 caused the peak shifts of only several residues, strongly suggesting that compound 6 causes only local perturbation in the structure of Bcl-$X_L$ but not to overall fold of Bcl-$X_L$. Furthermore, most of the residues whose chemical shifts are affected by the binding of compound 6 were around the BH3 binding pocket of Bcl-$X_L$. Therefore, the NMR HSQC experiments conclusively showed that compound 6 binds to the BH3 binding site in Bcl-$X_L$ and doesn't unfold the protein.

Example 12

In Vivo Antitumor Activity Experiments

The human breast cancer model is established in nude mice. BALB/c female nude mice (nu/nu) are obtained from Taconic Inc. Mice are 4-6 weeks old. All manipulations are performed under sterile condition. Tumor xenografts are established by injecting MDA-MD-231 cells ($1 \times 10^6$ cells) into two side pads. Tumors are measured with a caliper in three dimensions, length, width and high. Tumor volumes are calculated by (length×width×high). Treatments are initiated on day 7 post inoculation; the largest diameter reaches 5-7 mm and volume reaches 40 $mm^3$ at this time.

Bcl-2 small molecule inhibitors are used alone or in combination with other chemotherapy agents, for example, Docetaxel (Taxotere, TXT), Paclitaxel (taxol, tax), Cisplatin, 5-FU, Doxrubincin, epipodophyllotoxin (VP-16) and cyclophosphamide in mice bearing transplanted MDA-MB-23 tumors for determining the efficacy dosage for this tumors. Sub-optimal dose selected and used in combination studies are Docetaxel at 7.5 mg/kg or 3.75 mg/kg intravenously (i.v.) once a week; Paclitaxel (taxol, tax) at 7.5 mg/kg, three times per week intraperitoneally (i.p.); Cisplatin at 10 mg/kg, ip. once a week; 5-FU 10 mg/kg, three times per week i.p.; Doxrubincin 4 mg/kg, twice a week i.p.; epipodophyllotoxin (VP-16) 80 mg/kg, once a week i.p.; cyclophosphamide at 100 mg/kg, once a week i.p. The combination treatments are performed for 3 weeks.

The doses of the Bcl-2 inhibitors small molecule inhibitors of the present invention preferably range from 1 mg/kg to 100 mg/kg, daily or twice a week, administered in 0.1 ml i.p. for 3 weeks. Approximate tumor sizes and body weight are measured twice a week. Average volumes and standard deviations are calculated for each group and plotted.

For treating large tumors, the tumors are established as described above. Treatment is started on days 12, and on day 21, and the tumor's largest diameter reached 6-10 mm and 10-15 mm, and tumors volume reached volume of 93.2 and 559 $mm^3$, respectively.

For histological and Western analysis, the animals are sacrificed after treatment with the appropriate ODN's at the indicated concentration, and tumor are removed at various times from day 2 to day 18 following treatment for the purpose of detecting Bcl-2 level and for histologic examination. Twelve time points are preferably selected at 40 hrs, 48 hrs, day 3, 4, 6, 9, 10, 11, 14, 16, 17 and day 18. Tumor tissue samples collected from mice are fixed in 10% Formalin solution, and then embedded in paraffin blocks, from which 4 μm sections are cut and stained with Hematoxylin and Eosin (HE).

Statistical Analysis

The antitumor activity curves for the Bcl-2 small molecule inhibitors are plotted with the observation time on the X-axis, and corresponding tumor volume (geometric mean) on the Y-axis. The area under the curve (AUC) was calculated by Tai's mathematical model for each curve, and is shown as geometric means and 95% Otidencial interrals. The difference of AUC among treatment groups is compared by ANOVA.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

from the group consisting of hydrogen, $(C_1$-$C_6)$-alkyl, $(C_2$-$C_6)$-alkenyl, $(C_3$-$C_8)$-cycloalkyl, phenyl and trifluoromethyl; $A_1$ and $A_2$ are each independently 1 to 3 substituents selected from the group consisting of hydrogen, hydroxy, branched or straight chain $(C_1$-$C_6)$-alkyl, branched or straight chain $(C_2$-$C_6)$-alkenyl, $(C_3$-$C_8)$-cycloalkyl, phenyl, aryl, $(C_1$-$C_6)$-alkoxy, $CZ_3$ (wherein Z is selected from the group consisting of F, Cl, Br and I), $NH_2$, $NH((C_1$-$C_6)$-alkyl), $N((C_1$-$C_6)$-alkyl)$_2$, $NO_2$, CN, COOH, $COO(C_1$-$C_6)$-alkyl, $CONH_2$, $CONH(C_1$-$C_6)$-alkyl, $CON((C_1$-$C_6)$alkyl)$_2$, O—$(C_1$-$C_6)$-alkyl (where one, more than one or all hydrogen(s) in the alkyl radicals may be replaced by fluorine, or one hydrogen may be replaced by OH, $OC(O)CH_3$, $OC(O)H$, O—$CH_2$—Ph, $NH_2$, $NH((C_1$-$C_6)$-alkyl), $N((C_1$-$C_6)$-alkyl)$_2$, NH—CO—$CH_3$, or $N(COOCH_2Ph)_2)$, $SO_2$—$NH_2$, $SO_2NH(C_1$-$C_6)$-alkyl, $SO_2N((C_1$-$C_6)$-alkyl)$_2$, S—$(C_1$-$C_6)$alkyl, S—$(CH_2)_n$-phenyl, SO—$(C_1$-$C_6)$-alkyl, SO—$(CH_2)_n$-phenyl, $SO_2$-$(C_1$-$C_6)$-alkyl, $SO_2$-$(CH_2)_n$-phenyl (where n is 0-6 and the phenyl radical may be substituted up to two times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH((C_1$-$C_6)$-alkyl), $N((C_1$-$C_6)$-alkyl)$_2$), $NH(C_1$-$C_7)$-acyl, phenyl, biphenylyl, O—$(CH_2)_n$-phenyl (where n is 0-6), 1- or 2-naphthyl, 2-, 3-, or 4-pyridyl, 2- or 3-furanyl, 2- or 3-thienyl (wherein the phenyl, biphenylyl, naphthyl, pyridyl, furanyl, and thienyl rings may be optionally substituted up to 3 times by F, Cl, Br, I, OH, $CF_3$, $NO_2$, CN, $OCF_3$,

What is claimed is:

1. A pharmaceutical composition for modulation of apoptosis in a subject, comprising one or more anticancer agents and a therapeutically effective amount of a compound of formula:

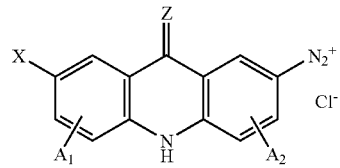

wherein, Z is O or S; X is selected from the group consisting of hydrogen and OR, wherein R is selected O—$(C_1$-$C_6)$-alkyl, $(C_1$-$C_6)$-alkyl, $NH_2$, $NH(C_1$-$C_6)$-alkyl, $N((C_1$-$C_6)$-alkyl)$_2$, $SO_2$—$CH_3$, COOH, COO—$(C_1$-$C_6)$-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position 1 or 2 by methyl or benzyl); and pharmaceutically acceptable salts and derivatives thereof; and a pharmaceutically acceptable carrier;

wherein said compound is present in an amount effective to modulate apoptosis in a subject.

2. The pharmaceutical composition of claim 1, wherein said modulation of apoptosis comprises promoting apoptosis.

3. The pharmaceutical composition of claim 1, wherein said compound is:

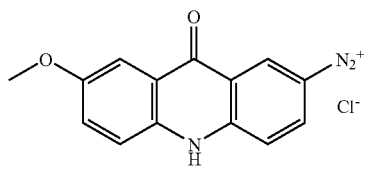

or pharmaceutically acceptable salts thereof.

4. The composition of claim 1, wherein said one or more anticancer agents are selected from the group consisting of docetaxel, paclitaxel, cisplatin, 5-FU, tamoxifen, doxorubicin, epipodophyllotoxin, and cyclophosphamide, or combinations thereof.

5. The composition of claim 1, wherein said anticancer agent is tamoxifen.

6. The composition of claim 1, wherein said anticancer agent is docetaxel.

7. A method for modulating apoptosis in a subject comprising administering to said subject in need thereof a therapeutically effective amount of a pharmaceutical composition of claim 1.

8. The method of claim 7, wherein said subject is a mammal.

9. The method of claim 8, wherein said mammal is a human.

10. The method of claim 7, wherein the amount administered is from about 0.1 mg/kg to about 1000 mg/kg.

11. The method of claim 10, wherein the amount administered is from about 0.5 mg/kg to about 500 mg/kg.

12. The method of claim 11, wherein the amount administered is from about 1 mg/kg to about 100 mg/kg.

13. The method of claim 7, wherein said compound is administered daily.

14. The method of claim 7, wherein said compound is administered twice a week.

15. The method of claim 7, wherein said compound is administered orally, intraorally, rectally, parenterally, epicutaneously, topically, transdermally, subcutaneously, intramuscularly, intranasally, sublingually, intradurally, intraocularly, intrarespiratorally, intravenously, intraperitoneally, intrathecally, by oral inhalation, or nasal inhalation.

16. The method of claim 7, wherein said compound is administered in dosage forms selected from the group consisting of tablets, pills, troches, dispersions, suspensions, solutions, capsules, patches, syrups, wafers, elixirs, gels, powders, magmas, lozenges, ointments, creams, pastes, plasters, lotions, discs, suppositories, nasal sprays, oral sprays and aerosols.

17. The method of claim 7, wherein said one or more anticancer agents are selected from the group consisting of docetaxel, paclitaxel, cisplatin, 5-FU, doxorubicin, epipodophyllotoxin, and cyclophosphamide, or combinations thereof.

18. The method of claim 17, wherein said chemotherapeutic drug is docetaxel.

19. The method of claim 7, wherein said modulating apoptosis comprises promoting apoptosis in a cell line selected from the group consisting of MCF-7, MDA-231, MDA-361, MDA-468, BJ474, MDA-435, HL-60 and T47C.

20. The method of claim 7, wherein said compound is:

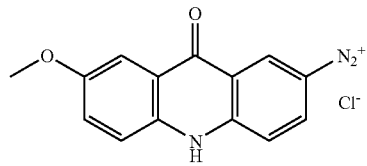

or pharmaceutically acceptable salts thereof.

* * * * *